(12) United States Patent
Viirre et al.

(10) Patent No.: US 7,572,234 B2
(45) Date of Patent: Aug. 11, 2009

(54) EEG FEEDBACK CONTROLLED SOUND THERAPY FOR TINNITUS

(75) Inventors: Erik Viirre, San Diego, CA (US); Jaime A. Pineda, San Diego, CA (US); John D. Hestenes, Blackhawk, CA (US); Andrey Vankov, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 380 days.

(21) Appl. No.: 11/292,266

(22) Filed: Nov. 30, 2005

(65) Prior Publication Data

US 2006/0167376 A1 Jul. 27, 2006

Related U.S. Application Data

(62) Division of application No. 10/276,018, filed as application No. PCT/US02/03866 on Feb. 5, 2002, now Pat. No. 7,081,085.

(60) Provisional application No. 60/266,553, filed on Feb. 5, 2001.

(51) Int. Cl.
*A61B 5/00* (2006.01)
*A61B 5/04* (2006.01)

(52) U.S. Cl. .................. 600/559; 600/300; 600/544

(58) Field of Classification Search ............ 600/544, 600/545, 559, 28; 607/2, 55; 73/585
See application file for complete search history.

(56) References Cited

U.S. PATENT DOCUMENTS

| 4,222,393 | A | | 9/1980 | Hocks et al. |
| 4,321,427 | A | * | 3/1982 | Singh .................... 73/585 |
| 5,403,262 | A | * | 4/1995 | Gooch .................... 600/28 |
| 5,601,091 | A | * | 2/1997 | Dolphin .................. 600/559 |
| 6,078,838 | A | | 6/2000 | Rubinstein |
| 6,210,321 | B1 | | 4/2001 | Di Mino |
| 6,234,979 | B1 | | 5/2001 | Merzenich |
| 6,631,295 | B2 | * | 10/2003 | Rubinstein et al. ........ 607/55 |

\* cited by examiner

*Primary Examiner*—Max Hindenburg
*Assistant Examiner*—Adam J Eiseman
(74) *Attorney, Agent, or Firm*—DLA Piper LLP (US)

(57) ABSTRACT

An automated method for treating tinnitus by habituation through use of neurological feedback, comprising the steps of connecting a subject through a set of attached headphones to an electronic sound player that is connected to a PC workstation presenting sound examples by software to the subject who can refine them by manipulating a series of controllers on the player, making an electronic recording of the sound in a digital music format, storing the recording in the computer, transferring a copy of the electronic sound file to the subject's electronic music player, generating an EEC signature of the subject's brain activity in response to the presented sound, sound using the customized sound to stimulate the auditory system while the brain activity is recorded, wherein the computer continuously monitors for the feedback signatures and drives the sound stimuli appropriately.

15 Claims, 15 Drawing Sheets

EEG FEEDBACK CONTROLLED SOUND THERAPY FOR TINNITUS

CROSS REFERENCE TO RELATED APPLICATIONS

This application is a divisional application of U.S. Ser. No. 10/276,018, filed Oct. 28, 2004; now U.S. Pat. No. 7,081,085 which is a 35 USC §371 National Stage application of PCT Application No. US02/03866 filed Feb. 5, 2002; which claims the benefit under 35 USC §119(e) to U.S. Application Ser. No. 60/266,553 filed Feb. 5, 2001, now abandoned. The disclosure of each of the prior applications is considered part of and is incorporated by reference in the disclosure of this application.

BACKGROUND OF THE INVENTION

1. Field of the Invention

The present invention generally concerns the diagnosis and treatment of tinnitus. The invention more specifically relates to the use of custom designed sound and feedback to determine the precise treatment sound matching the tinnitus, its neurophysiological effect, and monitoring the treatment effect by feedback from the brain.

2. Description of Related Art

Commonly perceived as a "ringing in the ear," tinnitus is a very frequent disorder of the auditory system, affecting about 17% of the general population and up to 33% in the elderly. About a quarter of these people are sufficiently bothered by their tinnitus that they seek professional help [Jastreboff et al, 1996]. Tinnitus is a phantom perception and thus not associated with any auditory stimulus. Until very recently, there were no objective measurements that could be related to tinnitus [Jastreboff et al, 1994], and diagnosis of tinnitus had to rely on various questionnaires, e.g. [Wilson et al, 1991]. The fact that tinnitus is perceived as a sound, however, indicates that it is associated with aberrant neural activity in the auditory pathways. Furthermore, the fact that tinnitus is associated with perception leads to the conclusion that central auditory structures such as the thalamus and auditory cortex must be involved. Neural correlates of tinnitus have indeed been found in central auditory structures [Norena et al, 1999; Mühlnickel et al, 1998; Wallhäusser-Franke et al, 1996]. Previously, tinnitus had been viewed as being caused in the auditory periphery [Eggermont, 1990; Tonndorf, 1981; Salvi and Ahroon, 1983], and even though neuronal activity related to tinnitus has been found in the central auditory system rather than in the periphery, it remains possible that the chain of events that leads to the development of tinnitus may be set off by events taking place in the periphery.

A Thalamic Model of Tinnitus

The presence of tinnitus-related neural activity in the central auditory system agrees well with a recently proposed neurophysiological model of tinnitus [Jeanmonod et al, 1996]. According to the model, tinnitus arises in the thalamus. Several parts of the thalamus interact to establish a reverberating loop. Neuronal activity originating from this reverberating loop is transmitted to the auditory cortex, where it gives rise to the tinnitus perception. This reverberating loop is established by disinhibition of neurons in the thalamus, which occurs when thalamic neurons receive inhibitory input causing a hyperpolarization. These thalamic neurons are capable of generating action potentials, once the hyperpolarization has reached a threshold. Thus, inhibitory input can cause these neurons to fire. The action potentials generated by this mechanism are called low threshold spikes (LTS) and usually occur in rhythmic bursts.

Two structures in the thalamus receive afferent auditory input: the medial geniculate body (MGB) and the multimodal medial thalamus (MT). Both these nuclei give excitatory input to the thalamic reticular nucleus (RT), and in turn receive inhibitory input from the RT. When afferent input into the MGB is normal, an equilibrium of excitation and inhibition is present in both MT and MGB. When the afferent auditory input into the thalamus fails, an imbalance of input is created. The MGB will receive no input whereas the MT receives a slightly decreased input. In this situation, the RT will still receive excitatory input from the MT, enough to generate the inhibitory output to both MT and MGB. Since no excitation is present in the MGB, the inhibitory input from the RT will hyperpolarize the neurons in the MGB. Neurons in the MGB will respond to this hyperpolarization with deinactivation leading to LTS bursts that are propagated to the auditory cortex.

Damage to the basilar membrane can set off the thalomocortical reverberating loop.

This model explains the appearance of tinnitus in conditions where the MGB is not receiving sensory input, e.g. in silent environments, or when hearing thresholds are temporarily or permanently raised after noise exposure. According to this model, once input into the MGB is restored, the tinnitus should vanish. Clearly, this is not the case in those people who are so annoyed by their tinnitus that they seek professional help. An additional mechanism must be in place to make tinnitus persist.

It has been noted that the presence of tinnitus cannot be determined from an audiogram, i.e. tinnitus may be present even when the MGB is receiving normal sensory input. The perception of tinnitus will only be stabilized when the person perceiving the phantom noise pays attention to it and associates it with unpleasant emotions [Jastreboff et al, 1996b; Langner and Wallhäusser-Franke, 1999] (FIG. 1). In this scenario, the person experiencing tinnitus is annoyed by it. Consequently, he will direct his attention to the phantom sound, thereby activating the limbic system. The limbic system is assumed to give rise to an increased generation of tinnitus-related activity. The detection of tinnitus-related activity is facilitated by mechanisms of lateral inhibition in the central auditory system. These will act to confine the phantom sound to regions representing distinct frequencies and increase the contrast between the tinnitus-related activity in these regions and the spontaneous activity in adjacent regions. This will lead to increased tinnitus perception. The increased perception can then lead to increased annoyance, completing a positive feedback cycle that will make tinnitus persistent.

The Auditory N100 as an Index of Cortical Responsiveness

Event-related potential (ERP) studies have demonstrated that electrical activity time-locked to stimulus or response events and averaged over repeated trials reflects information processing in the cortex [Hillyard et al, 1978; Pritchard, 1981b; Duncan-Johnson and Donchin, 1977; Pinedaetal, 1997; Pineda et al, 1998]. Considerable evidence to date indicates that long-latency potentials (approximately >100 ms poststimulus) appear primarily sensitive to cognitive variables that reflect task requirements and the psychological state of the subject. These "endogenous" potentials most likely reflect non-obligatory activities invoked by the demands of the task.

One of the most widely studied endogenous components is the N100. Wolpaw and Penry [Wolpaw and Penry, 1975] were the first to propose that the N100 consisted of midline and temporal subcomponents. Subsequent work has shown that midline components can be modeled with tangential generators on the superior temporal plane and pointing toward the midline of the scalp. At least two midline components have been distinguished. An early frontocentral peak (N100a) shows reliable tonotopic changes in distribution and sensitivity to attention [Woods, 1995]. A later midline component (N100b) shows the same distribution for tones of different frequency.

N100 components show increases in amplitude and decreases in latency with increasing stimulus intensity [Hillyard et al, 1978; Scherg and von Cramon, 1990; Mäkelä and Hari, 1990]. In some individuals, the increases in stimulus intensity often bring decreased amplitude and increased latency. This tendency for N100 to increase or decrease in magnitude in response to stimuli of increasing intensity has been called the "augmenting/reducing" (AR) response. These intensity-amplitude functions have been hypothesized to result from variations in the central modulation of sensory processing and/or the actions of nonspecific arousal systems [Zuckermann et al, 1974; von Knorring and Perris, 1981]. It has also been proposed that they may reflect the "tuning" properties of a cortical gating mechanism that regulates sensory input [Buchsbaum and Silverman, 1968; Lukas and Siegel, 1977; Pritchard et al, 1985]. Some have related this mechanism to "attention" shifts and "overload" protection at high stimulus intensities.

A number of studies have shown that midline auditory N100 shows strong intensity dependence, while those recorded from temporal electrodes show weak intensity dependence [Pineda et al, 1991]. These differences suggest different N100 generators in the primary and secondary auditory areas [Pineda et al, 1991] [Connally, 1993], which is consistent with the multiple N100 generator hypothesis [Woods, 1995].

How Thalamo-Cortical Activity Affects the A/R-Response

The rhythmic LTS bursting activity of thalamic neurons mentioned above is also observed in slow wave sleep [Pape and McCormick, 1989; Steriade and Llinas, 1988], where it is thought to be a gating mechanism blocking sensory input into the cortex [Pape and McCormick, 1989; Steriade and Llinas, 1988]. The argument has also been made that this mechanism is active not only during sleep but also during waking and may result in different attentional states. The excitation of cortical tissue by tinnitus may compete with stimulus-induced activity. The neural activity induced by the tinnitus may, therefore, be regarded as competition for cortical neuronal substrates. This may lead to the reorganization of the auditory cortex [Mühlnickel et al, 1998]. That is, the processing of stimuli in the presence of tinnitus-related activity may lead to increases in the firing rate of neurons, the use of more neural substrate, or a combination of both. It is hypothesized that these mechanisms for dealing with tinnitus-related activity in the auditory system lead to the increased intensity dependence of the auditory evoked potential that Inventors and others have observed [Norena et al, 1999].

The hypothesis that tinnitus-related neural activity is caused by oscillatory LTS activity in the thalamus is further supported by a combination of other findings. First, application of serotonin in the lateral geniculate body (LGB) or MGB of the cat suppresses the hyperpolarization necessary to generate LTS-bursts [Pape and McCormick, 1989]. Second, the intensity dependence of the auditory evoked potential is strongly influenced by brain serotonergic activity [Juckel et al, 1999; Juckel et al, 1997; Hegerl et al, 1996]. Finally, these observations are linked by the fact that the thalamus contains a high density of binding sites for serotonergic drugs as well as serotonin uptake sites [Smith, 1999].

Elaboration on the Tinnitus Models

Taken together the various models and evidence suggest that while tinnitus may be triggered by events in the periphery, the mechanisms that make tinnitus a persistent and annoying condition are located in the central auditory system. Furthermore, it appears that people suffering from tinnitus unintentionally train themselves to have tinnitus by using negative reinforcement. It has been shown that the cortical representation of tones associated with unpleasant sensations is enlarged [Gonzalez-Lima and Scheich, 1986] and/or changed to enhance the contrast between this particular tone and other tones of similar frequency [Ohl and Scheich, 1996]. The cortical representation of tones no longer associated with unpleasant sensations will return to a state where contrasts are no longer enlarged. Moreover, responses to stimuli occurring while attention is directed at another task will decrease over time [Anderson and Oatman, 1980]. This suggests that if the association between tinnitus and unpleasant emotions can be broken, the aberrant neuronal activity in the central auditory system can be decreased by habituation. Then tinnitus is treated like any other sound that does not carry relevant information: it is ignored. The tinnitus retraining therapy (TRT) introduced by Jastreboff [Jastreboff et al, 1996a] makes use of the mechanism described above. However, TRT as described by Jastreboff uses white or broadband noise as a habituating stimulus. The rationale behind the use of white noise is to generate a decreased signal-to-noise ratio between the tinnitus-related neuronal activity and random background activity in the auditory system. This would be achieved by introducing a quasi-random, stimulus-driven activity into all of the parallel tonotopic channels of the auditory system.

A precise computational model of tinnitus has been proposed by Langner et al [Langner and Wallhäusser-Franke, 1999] based on animal work. This model assumes that the limbic system is necessary for stabilizing the tinnitus perception. It also explains how a decreased auditory input resulting from a peripheral hearing deficit can give rise to a specific tinnitus pitch. When the tinnitus sound is used as a habituation stimulus, Langners' model predicts the tinnitus would disappear.

Currently, there are sound therapies for tinnitus that use generic sounds. These present therapies are only partially effective and require a long time for treatment. It would, therefore, be desirable to obtain a brain signal feedback system, wherein one could rapidly suppress brain activity related to tinnitus and provide relief for this disorder.

SUMMARY OF THE INVENTION

To address the beforementioned problem and the above solution the inventors disclose their invention as follows.

The invention contemplates an automated method for treating tinnitus by habituation to customized sound through use of neurological feedback. The methodology comprises the following steps. The tinnitus-suffering subject is connected through headphones to an electronic sound player that in turn is connected to a PC workstation. A customized sound profile is created for the subject's particular tinnitus by presenting a plurality of audible sound examples from a tinnitus sound library in special software. The subject is allowed to choose and refine the presented sounds that most closely resemble his or her tinnitus sound. The refined sound is recorded in a digital music format to create a custom sound profile for that particular subject, and the custom sound profile recording is stored in a computer.

An EEG signature of the subject's brain activity in response to the presented sound is generated by downloading a copy of the electronic sound file to the subject's electronic music player, presenting custom sound most closely matching the tinnitus to stimulate the auditory system, and recording the subject's neurological response to sounds adjacent to but not specifically corresponding to his tinnitus signature. The subject's brain activity during absence of sound stimuli is also recorded. The EEG profile is uploaded into the computer to create the EEG signature. When undergoing treatment, the EEG response is actively monitored by the computer, which generates sound in response. The computer periodically tests the signatures for tinnitus and silence and determines if the tinnitus is decreasing and the silence signal is strengthening, and when if these desirable changes are not present, the computer slightly alters the sound stimuli and again checks for feedback. Thus, the computer continuously monitors for the feedback signatures and drives the sound stimuli appropriately to habituate the subject to his tinnitus.

A method is also contemplated by this invention for customized habituation treatment of tinnitus without masking sound or using subthreshold sound. This method involves matching narrowband sound frequency to a patient's perceived tinnitus and presenting the matched sound frequency to the subject, wherein the presented matched sound activates the same population of neurons affected by tinnitus, and wherein habituation occurs when the tinnitus and the habituating stimulus sound are as much alike as possible. Periodically, frequency changes are updated as required for maintaining maximum habituation.

An objective method for diagnosing tinnitus by detecting changes in the dynamic response characteristics of the auditory cortex induced by tinnitus is further contemplated. This method comprises characterizing a subject's tinnitus perception by matching the pitch of his or her tinnitus to the frequency of a pure sine tone generated by a function generator, having a programmable logarithmic amplifier that is controlled in real time by a stimulus presentation and data collection program software to set the intensity of each stimulus. An auditory evoked potential to a variety of tone pitches, including the tinnitus pitch is recorded, wherein the increased activation of the auditory cortex manifests itself as an increased slope of the AR. The slope of the AR response for tinnitus frequency tones is calculated, wherein an observed increase in the slope of the AR in tinnitus indicates tinnitus-related activity present in the auditory cortex.

Another preferred method for treating tinnitus by habituation to its sound frequency comprises the steps of determining the "matching frequency" (pitch) of a subject's tinnitus, determining the hearing threshold for the tinnitus frequency; determining the "matching intensity" of the subject's tinnitus, and determining the hearing threshold for the "off frequencies. This is followed by stimulating the auditory system in two series of tonal stimulation; first at the tinnitus frequency, and second at the "off frequency. EEG data is collected and the subject is given an electronic music player having the habituation stimulus downloaded into it. The subject is asked to listen to the player for as long as it is comfortable each day.

The "matching frequency" is determined by presenting the subjects with a continuous, audible tone varying in pitch, and asking them to indicate the frequency most closely matching the frequency of their tinnitus. To determine the threshold, subjects are presented with a continuous tone that gradually increases in volume, and are asked to indicate when they begin to hear the tone. The intensity at which the subjects begin to hear the tone is considered the hearing threshold. "Matching intensity" is determined when subjects are presented with a continuous tone that increases or decreases in volume and are asked to indicate the moment when they perceive the tone as being of the same loudness as their tinnitus.

An EEG marker of tinnitus suitable for diagnosing the presence of tinnitus is also contemplated by this invention. This marker comprises a replica of a subject's tinnitus sound experience and a measure of the subject's EEG response to increasing intensity of the sound. The replica of sound is constructed from a subject's subjective determination of sound most closely related to the annoying sound experienced by him, and the patient's EEG response is measured to determine peak amplitude of the N100 component.

These and other aspects and attributes of the present invention will become increasingly clear upon reference to the following drawings and accompanying specification.

DESCRIPTION OF THE PREFERRED EMBODIMENT

Introduction

Figure 1:
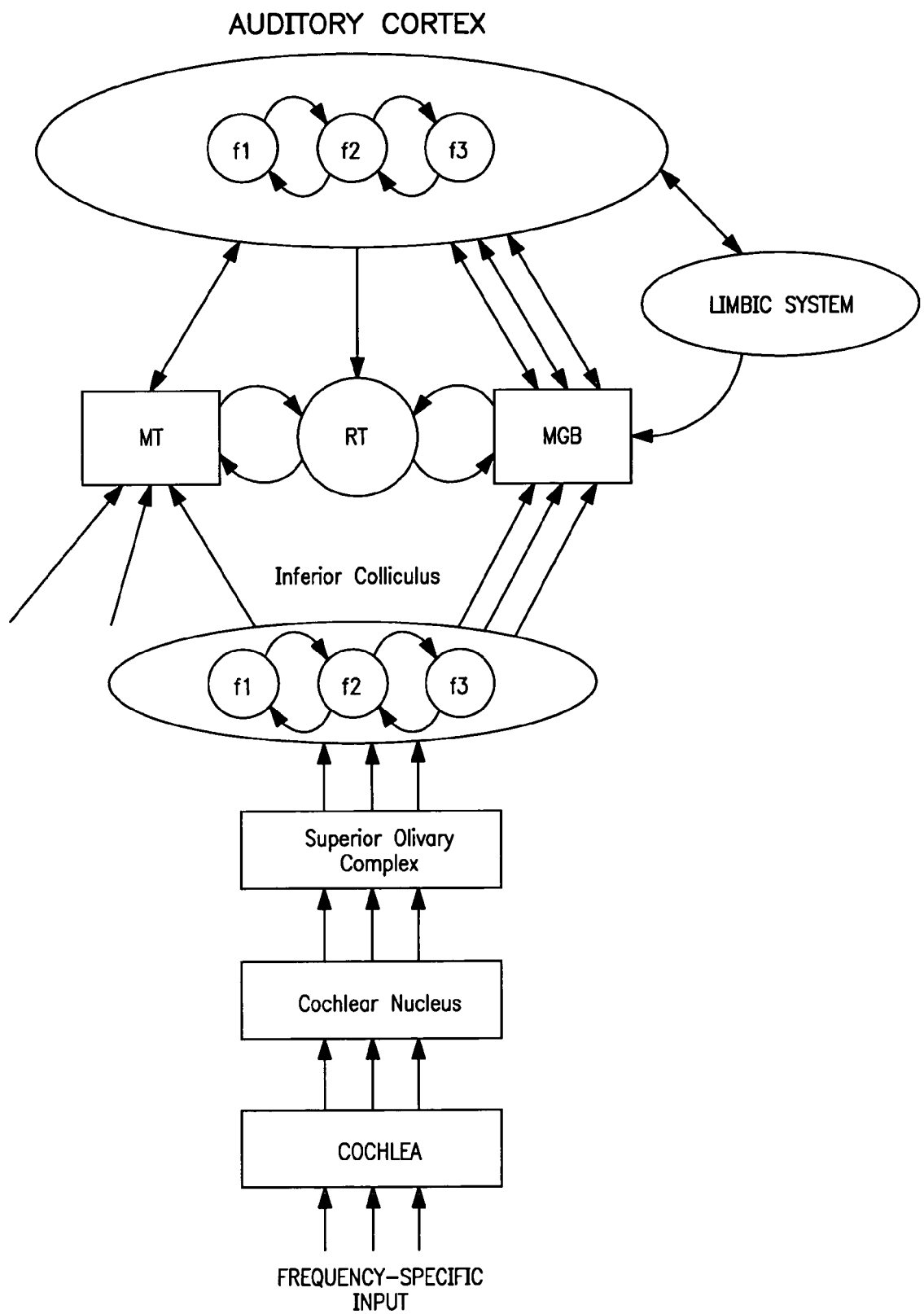
FIG. 1 is an overview of the auditory system with regard to tinnitus generation and the Mechanisms stabilizing tinnitus. Adapted from Jeanmonod 1996 and Langner 1999. Explanation is in the text.

Based on the aforementioned modes, Inventors devised a frequency-specific or custom-made habituation stimulus that sounds like the patient's tinnitus for habituation purposes. Such a stimulus activates the same population of neurons affected by tinnitus. It is Inventors' contention that habituation occurs when the tinnitus and the habituating stimulus sound are as much alike as possible.

The persistent activation of cortical tissue by tinnitus is assumed to compete for neural substrate with normal stimulus-induced activity in the primary auditory cortex. In order to compensate, the processing of auditory stimuli in the presence of tinnitus-related activity may require an increase in firing rate of neurons, the use of more neural substrate, or a combination of both. Inventors have hypothesized that these compensatory mechanisms lead to an increased intensity dependence in responses to external auditory events. Since the magnitude of the largest possible response is limited, the presence of tinnitus may lead to a steeper gain function in the responsiveness of the primary auditory cortex and a decrease in the dynamic range of hearing sensitivity.

A correlate of this steeper gain function has been reported by Norena and colleagues [Norena, 1999], who observed an increased intensity dependence of the N100 auditory evoked potential in tinnitus subjects. The N100 is known to increase in amplitude and decrease in latency with increasing stimulus intensity [Hillyard, 1978, Scherg, 1990, Mäkelä, 1990]. This intensity dependence of the N100 response is associated with the tangentially oriented dipole of the N100 component that is recorded primarily along midline sites. According to studies of dipole source analysis [Verkindt, 1995, Scherg, 1991], this tangentially oriented dipole reflects mainly activity of the primary auditory cortex. In contrast, the radially oriented dipole reflects activity of the secondary auditory cortex in the more lateral parts of the temporal lobe [Hegerl].

Since it is assumed that tinnitus-related activity involves the primary auditory cortex, the dependent measure for this study was the midline N100 component. This component appears to be a good index for tinnitus because it reflects stimulus properties as well as attention and the psychological state of the subjects, both of which are presumed to contribute to tinnitus [Jastreboff, 1996].

Since tinnitus perception is subjective by its very nature, there have been no objective measurements that could be related to it, until very recently [Jastreboff 1994]. A diagnosis of tinnitus has had to rely on a variety of questionnaires [Kuk 1990, Wilson 1991]. On the other hand, changes in the dynamic response characteristics of the auditory cortex by tinnitus could be used as a basis for an objective diagnostic tool.

The N100 component of the auditory evoked potential has been shown to be an indicator of activity in the central auditory system [Pritchard, 1981 a]; [Norena et al, 1999]; [Pineda et al, 1997; Pineda et al, 1998]. Because event-related potentials like the N100 are by definition evoked by physical stimuli, whereas tinnitus is not, event-related potentials can be used as more objective measures of tinnitus induced changes in the processing of tones rather than the tinnitus itself [Norena et al, 1999]. N100 shows reliable intensity dependence in both humans and non-human primates [Picton et al, 1976]; [Pineda et al, 1991]. That is, as sounds get louder, the magnitude of the response increases for many individuals, while it decreases for others. This has been called an augmenting/reducing (AR) response and is assumed to index the "tuning" properties of a cortical gating mechanism that regulates sensory input [Buchsbaum and Silverman, 1968]; [Lukas and Siegel, 1977]; [Pritchard et al, 1985]. Inventors' research program had two main specific aims:

1. devise an objective method for the detection of tinnitus, and
2. assess the efficacy of customized acoustic habituation therapy.

Tinnitus and Lateral Inhibition

EXAMPLE I

Tinnitus Causes Specific Changes to the Augmenting/Reducing Response

As Inventors have discovered in their own laboratory and has been shown elsewhere, tinnitus increases the slope of the AR response of the N100 component of the auditory evoked potential [Norena et al, 1999]. Furthermore, it has also been shown by means of magnetic source imaging that tinnitus induces tonotopically organized activity in the auditory cortex [Mühlnickel et al, 1998]. It was therefore hypothesized that the AR response at the specific frequencies at which tinnitus is perceived will have a steeper slope. Tinnitus patients match the pitch of their tinnitus to the frequency of a pure tone. The auditory evoked potential to a variety of tone pitches, including the tinnitus pitch, is then be recorded from patients and normal controls. The magnitude of N100 responses allows Inventors to calculate the slope of the AR response for tinnitus frequency tones, as well as for frequencies not related to tinnitus perception. In normal controls, the tinnitus match is be substituted with a 4 kHz tone, since audiograms show a precise hearing threshold for this frequency and it is also near the 4.2 kHz average of tinnitus matching frequencies determined in Inventors' pilot studies.

Inventors propose that the observed increase in the slope of the AR in tinnitus is due to tinnitus-related activity present in the auditory cortex. It is their contention that this activity interferes with stimulus driven activity in such a way that more cortical tissue has to be activated and that firing rates of individual cortical neurons have to be higher in order to allow for processing of peripheral stimuli. This increased activation of the auditory cortex manifests itself as an increased slope of the AR. Plastic changes mediated by a positive feedback loop involving structures in the limbic system and mechanisms of lateral inhibition in the auditory pathway may lead to the maintenance of the tinnitus experience. This line of argumentation links the thalamic model of Jeanmonod [Jeanmonod et al, 1996], which forms the basis for the proposal, and the changes in inventors' dependent variable.

Figure 2:
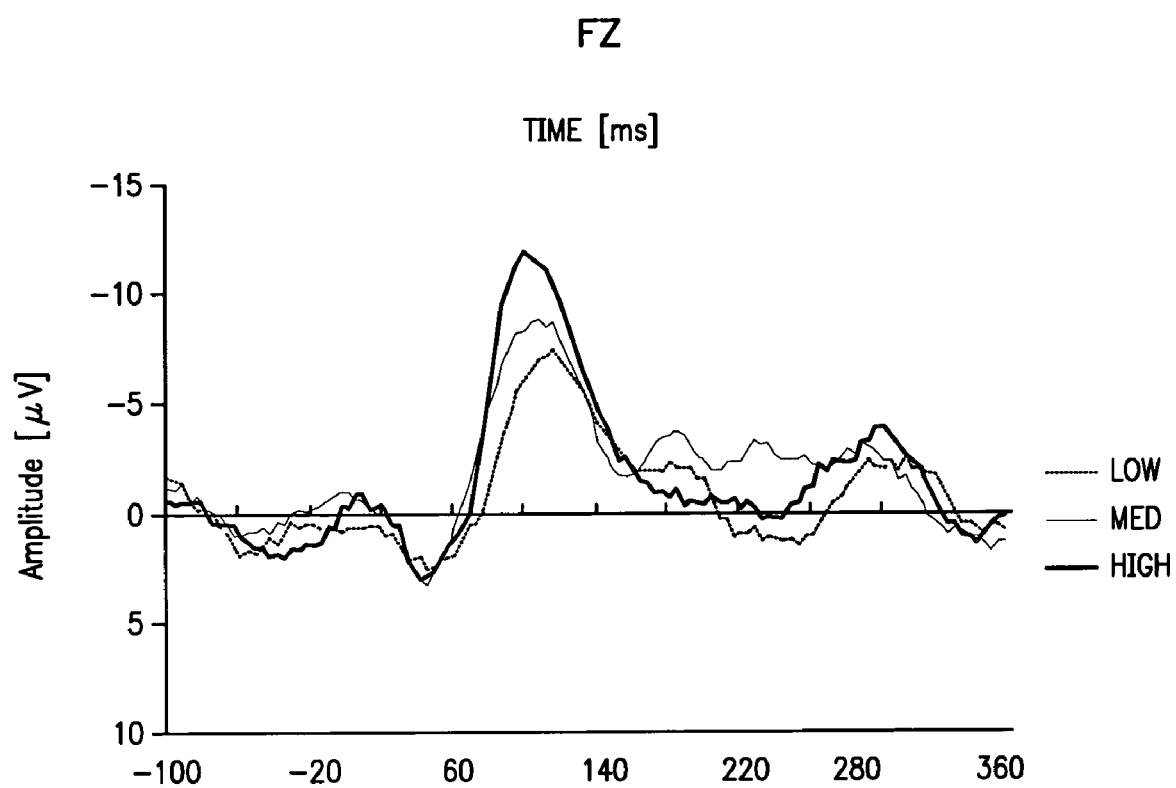
FIG. 2 displays the auditory-evoked potential at the electrode position Fz, recorded at 30 dB (LOW), 42 dB (MED) and 54 dB (HIGH) above the subject's hearing threshold. Note that the amplitude of the N100 component increases with increasing stimulus volume.

The first step towards a characterization of the augmenting/reducing response was to develop a method that allowed Inventors to reliably record the N100 component and separate it from background noise. The size of the N100 component is largely determined by the loudness of the stimulus. Since Inventors anticipated working with subjects that have some degree of hearing loss, they chose to use stimulus volume settings that correspond to the subjects' individual hearing thresholds rather than use the same predetermined volume settings for all subjects. This choice of volume settings should ensure that the perceived loudness of the stimuli is as similar as possible across subjects. If the stimulus is presented at 30 dB or more above the subject's hearing threshold at the stimulus frequency, the signal-to-noise ratio is sufficient to reliably detect the N100 component and to demonstrate it's dependence on stimulus intensity (FIG. 2).

Figure 3:
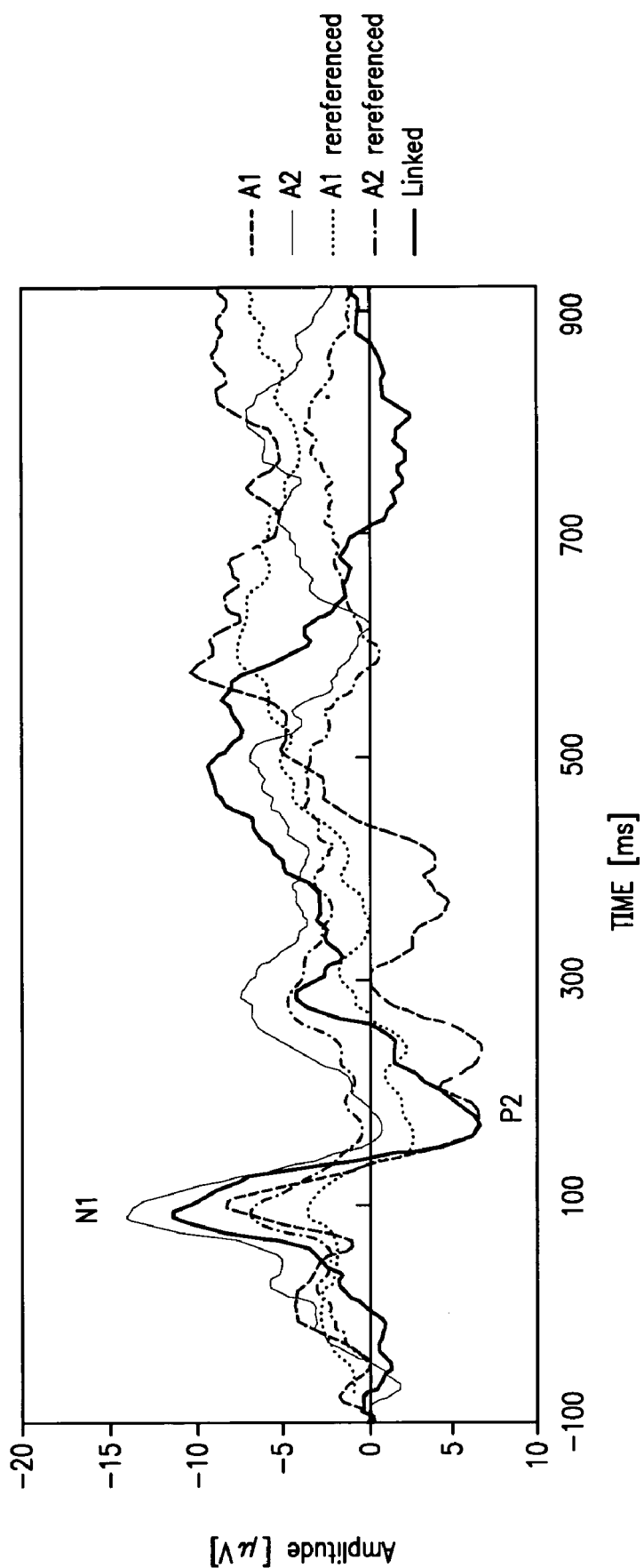
FIG. 3 shows the auditory-evoked potential at the electrode position Fz, recorded using various references. The stimulus was a 1 kHz tone presented at 54 dB above the subject's hearing threshold. The stimulus was presented 80 times in each condition.

Another factor that affects the ability to detect the N100 component is the placement of the reference electrodes. We, therefore, recorded the auditory evoked potentials comparing a number of different references, including a single mastoid, linked mastoid and the average reference method [Katznelson, 1981]. The results showed that the N100 component and the entire N100/P200 complex was seen most clearly using the linked mastoids as a reference. The recordings made with the linked mastoids reference is also the only one in which the wave form of the N100/P200 complex closely resembles the waveforms found in previous publications, e.g. [Picton et al, 1976] (FIG. 3). Because the N100/P200 complex was present at various electrodes, re-referencing the single mastoid recordings to the average potential of all electrodes partially cancelled the N100/P200 signal, worsening the signal-to-noise ratio.

Figure 4:
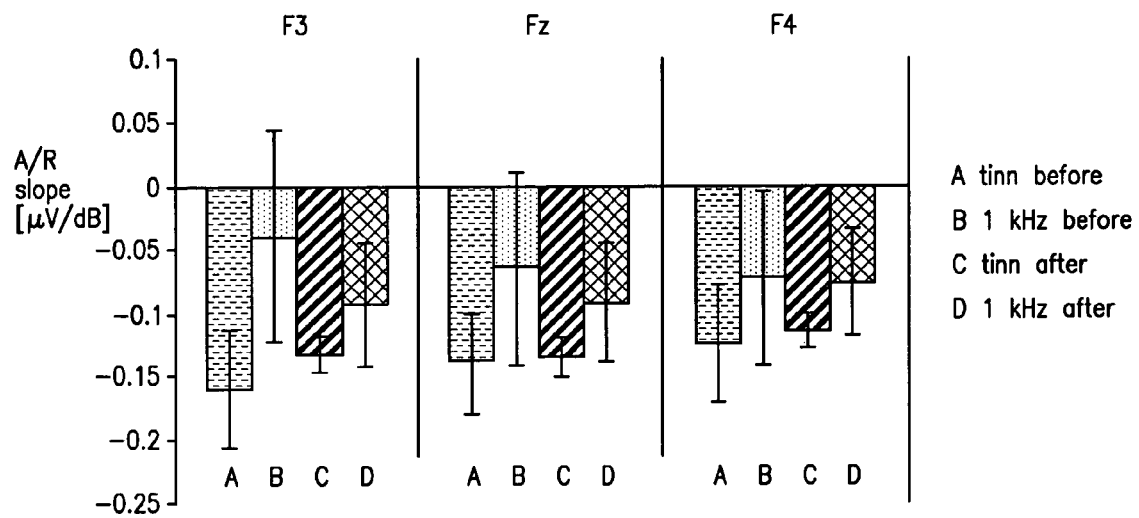
FIG. 4 demonstrates that the intensity dependence of both amplitude (top) and latency (bottom) the N100 component of the auditory evoked potential in tinnitus subjects is changed by one hour of habituation training. (N=4).
Figure 4:
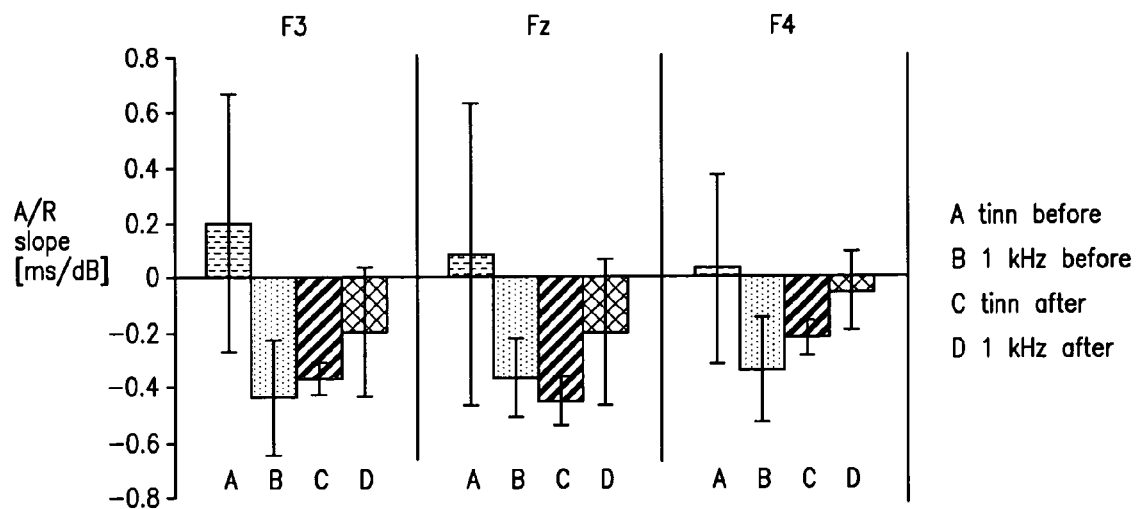

In another study, Inventors asked tinnitus subjects to match the pitch of their tinnitus to the frequency of a sine tone and recorded their auditory event-related potentials to tones of this frequency at 30 dB, 36 dB, 42 dB, 48 dB, and 54 dB above their individual hearing thresholds. The N100 amplitude in response to these tinnitus frequency tones showed a much larger intensity dependence than to 1 kHz tones. Likewise, N100 latencies increased with increasing stimulus volume (FIG. 4).

Figure 5:
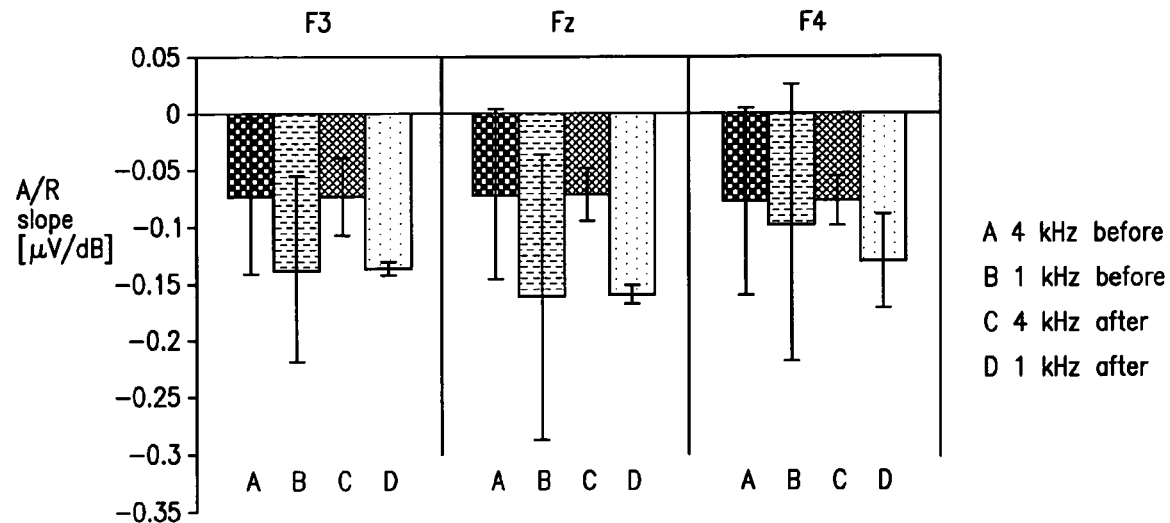
FIG. 5 reveals that neither the intensity dependence of amplitude (top) or latency (bottom) the N100 component of the auditory evoked potential in normal control subjects is affected by a one hour exposure to narrow band noise. (N=2)
Figure 5:
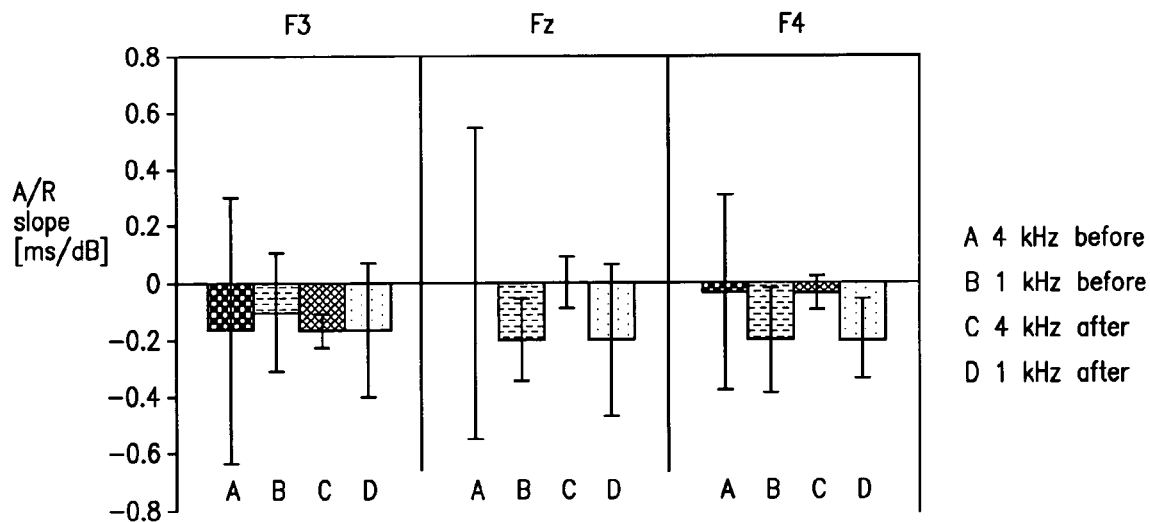
Figure 6:
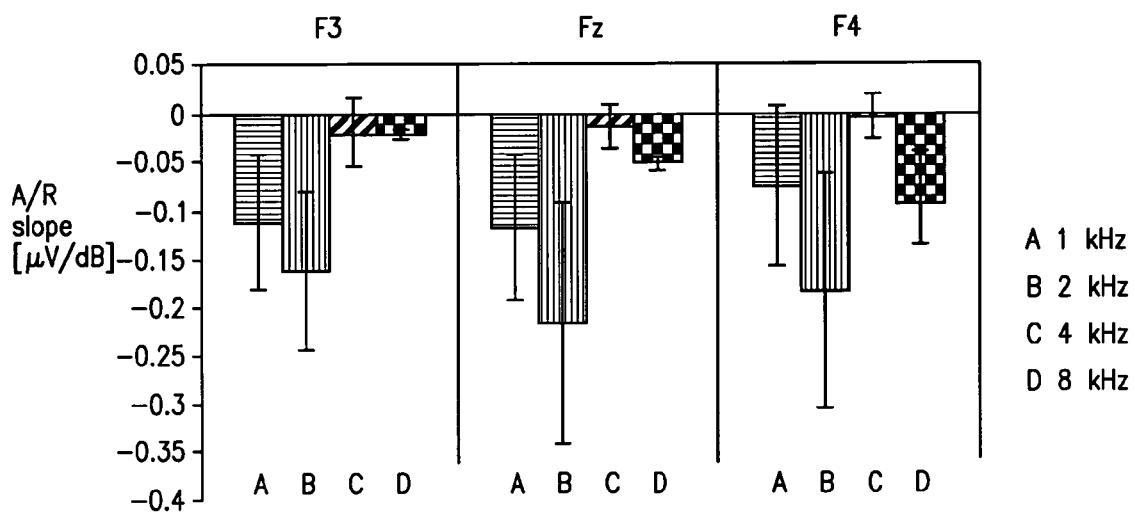
FIG. 6 further shows that the intensity dependence of the N100 component of the auditory evoked potential varies with stimulus frequency. Note that the A/R responses to 1 kHz tones are similar in normal control subjects and tinnitus subjects before habituation training (FIG. 5), whereas the A/R responses to 4 kHz tones in normal controls and the responses to the tinnitus frequency are in tinnitus subjects before habituation are very different. (N=3)
Figure 6:
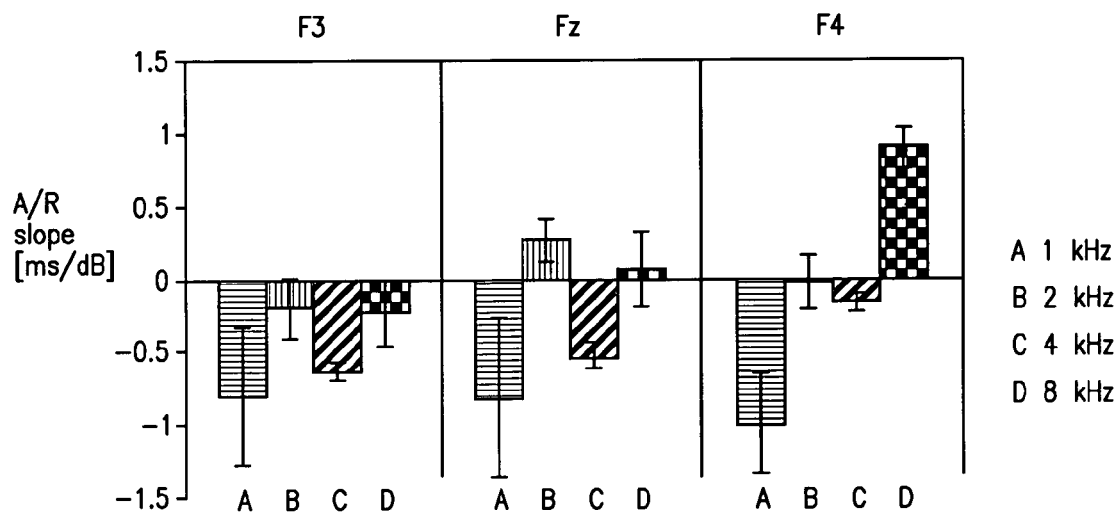

The responses to 2 kHz and 4 kHz (chosen to substitute for the tinnitus frequency) tones were recorded from normal listeners in two separate control experiments (FIG. 5 and FIG. 6). In the control subjects, the responses to 1 kHz tones were much more strongly intensity dependent than responses to 4 kHz tones, while the N100 latency to the 4 kHz tones decreased with increasing stimulus volume. Taken together these findings strongly suggest that tinnitus induces specific changes to the augmenting/reducing response.

Materials and Methods

Subjects

Eight subjects suffering from tinnitus (mean age: 46.8 yr.; S.D.=+11.7) and twelve control subjects (mean age: 39.1 yr.; S.D.=±10.7) were studied. The hearing thresholds of all subjects were determined using routine pure tone audiometry. Patients suffering from tinnitus were referred from the Head and Neck Surgery Clinic at the UCSD Medical Center, while control subjects were recruited from the population of the UCSD campus. An effort was made to match the age of the control subjects to the age of the tinnitus subjects. Informed consent was obtained from all subjects. The Institutional Review Board of the University of California, San Diego approved the experimental procedures.

Tinnitus Matching Procedure

A subject's tinnitus perception was characterized prior to every recording session by matching the pitch of their tinnitus to the frequency of a sine tone. In our experience, this matching procedure has proven vulnerable to octave confusions, i.e. some subjects matched their tinnitus pitch consistently at two different frequencies, depending on whether the matching procedure was begun at a frequency higher or lower than their tinnitus pitch. These frequencies generally were one or two octaves apart. If this was the case, we alternately presented both frequencies to the subject and asked which one was a better match.

EEG Experiments

EEG was collected using standard methods. Data were recorded from 15 electrode sites mounted on an elastic cap and located over the following scalp sites: F3, Fz, F4, C3, Cz, C4, P3, Pz, P4, T3, T4, T5, T6, O1, and O2 (according to the modified International 10-20 System). Eye movement artifact, particularly blinks, was recorded from vertical and/or horizontal EOG electrodes. In order to maintain compatibility with previous studie, all electrode sites were referred to linked mastoids. Within each series, 80 stimuli of different intensities, for a total of 400 stimuli, were presented in random order and at intervals varying randomly between 1 and 3 sec. The EEG was amplified by a factor of 10,000 and band-pass filtered between 0.01 to 100 Hz using 3 dB down filter skirts. Analog signals were recorded and digitized at a sampling rate of 250 Hz.

The auditory stimuli were pure tones generated by a function generator. A specially designed programmable logarithmic amplifier that was controlled in real time by a stimulus presentation and data collection program set the intensity of each stimulus. Tone pips of 200 ms duration were presented at five different intensities (30 dB SL, 36 dB SL, 42 dB SL, 48 dB SL and 54 dB SL) through insert earphones (Eartone 3A transducers with Earlink foam eartips). Inventors recorded auditory event-related potentials (ERP) in response to tones at three frequencies. For the tinnitus subjects these frequencies were 1 kHz, 2 kHz and their tinnitus-match frequency. In non-tinnitus subjects 4 kHz substituted for the tinnitus frequency.

Data Analysis

The EEG data were analyzed using a two-stage approach. In the first stage, traditional artifact rejection was employed to remove trials with amplifier blocking and those that contained eye movement artifacts. The artifact-free EEG epochs for each intensity and condition were then averaged and the amplitudes of the N100 components measured. Based on these data, intensity-amplitude functions were computed for all 15 electrode sites. These were used to characterize an individual's responsiveness to specific tonal frequencies.

The peak amplitudes of the N100 component were measured and plotted against the stimulus intensity. A linear regression was calculated, and its slope was used to characterize the intensity dependence of the N100 component recorded from the midline electrode sites Fz, Cz and Pz. For each stimulus frequency, these intensity-amplitude functions were compared between the tinnitus and control groups using a 2-tailed Wilcoxon-Mann Whitney U-test (p<0.05). Since three tests were performed for each stimulus condition, a correction for multiple comparisons based on the binomial distribution [Bortz, 1990] was performed by calculating $\alpha'$:

$$\alpha' = \sum_{i=n}^{k} \binom{k}{i} \alpha^i \cdot (1-\alpha)^{k-i}$$

where k was the number of tests performed, n the number of tests that showed a significant result and a the significance level of the individual tests. Differences in the intensity-amplitude functions were considered significant when $\alpha'$ was less than the desired significance level, i.e. $\alpha'<0.05$.

Results

Figure 11:
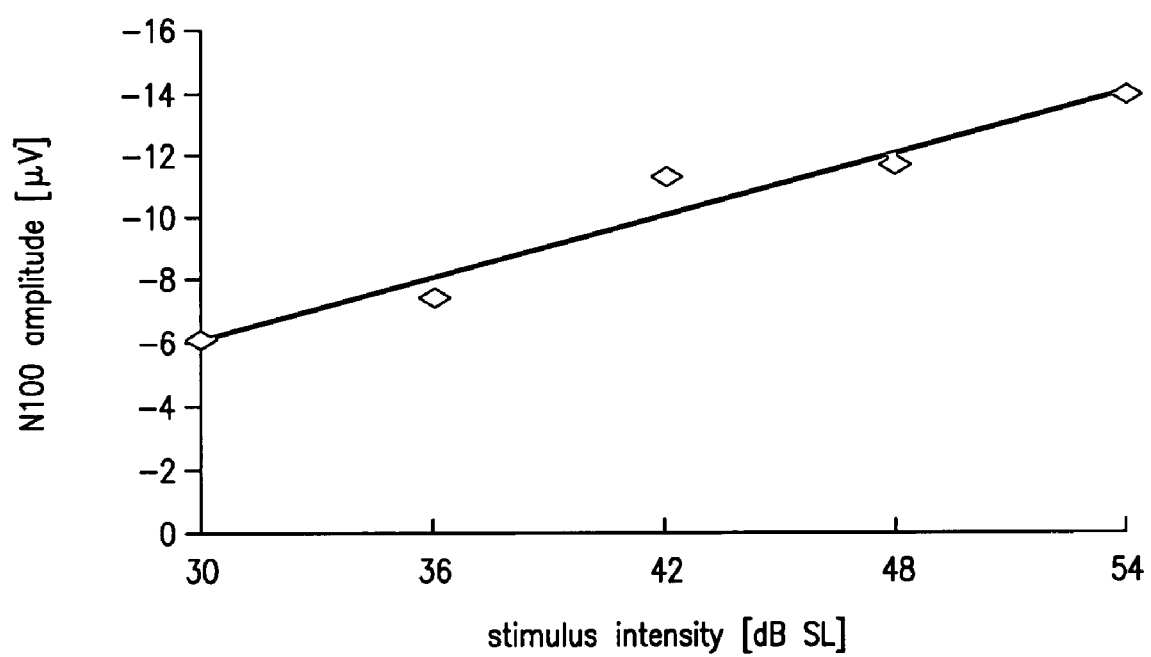
FIG. 11 shows an example of the N100 intensity dependence slope.
Figure 12A:
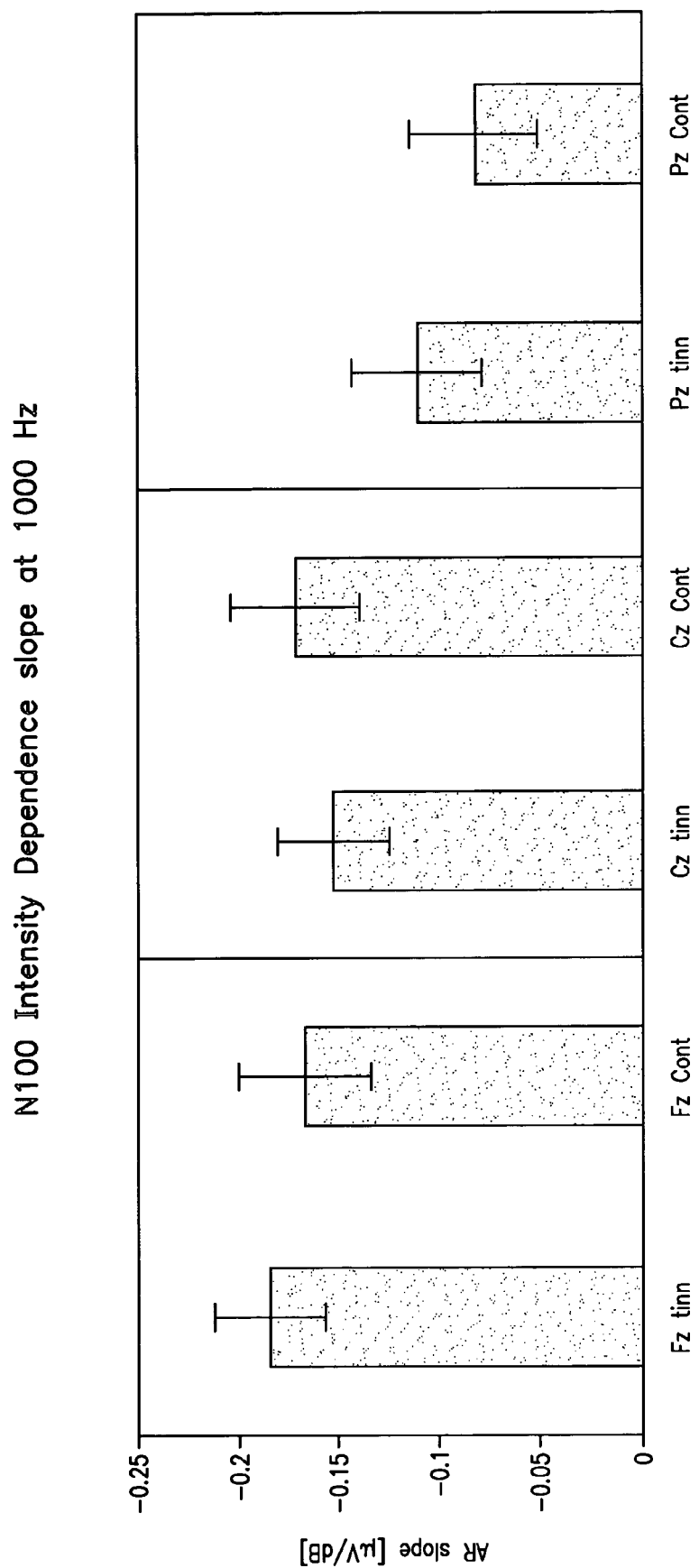
FIGS. 12A-12C are representations of N100 intensity dependence slopes for the 1 kHz, 2 kHz, and tinnitus/4 kHz tones, respectively, in tinnitus subject and controls. Only three midline sites (Fz, CZ, and PZ) are shown. (p<0.05, Wilcoxon-Mann-Whitney U-Test).
Figure 12B:
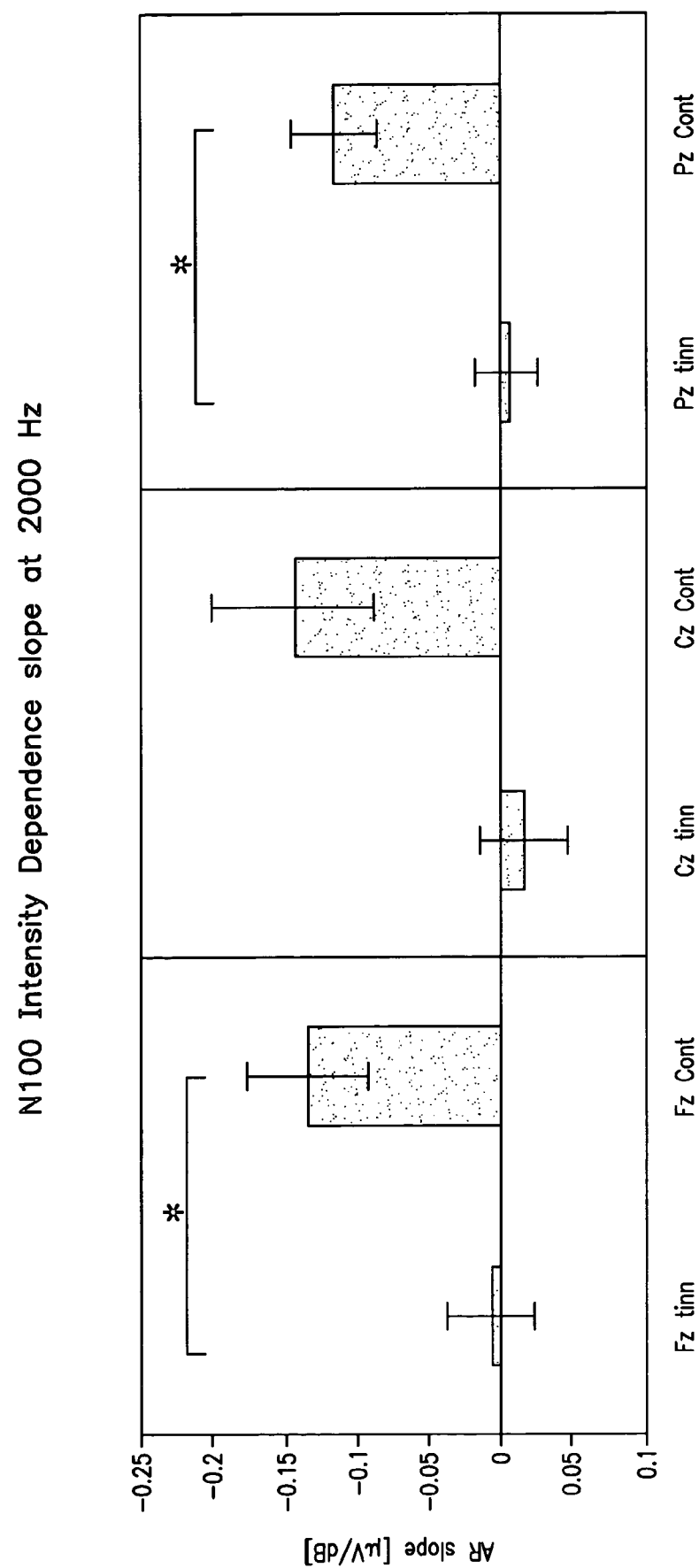
Figure 12C:
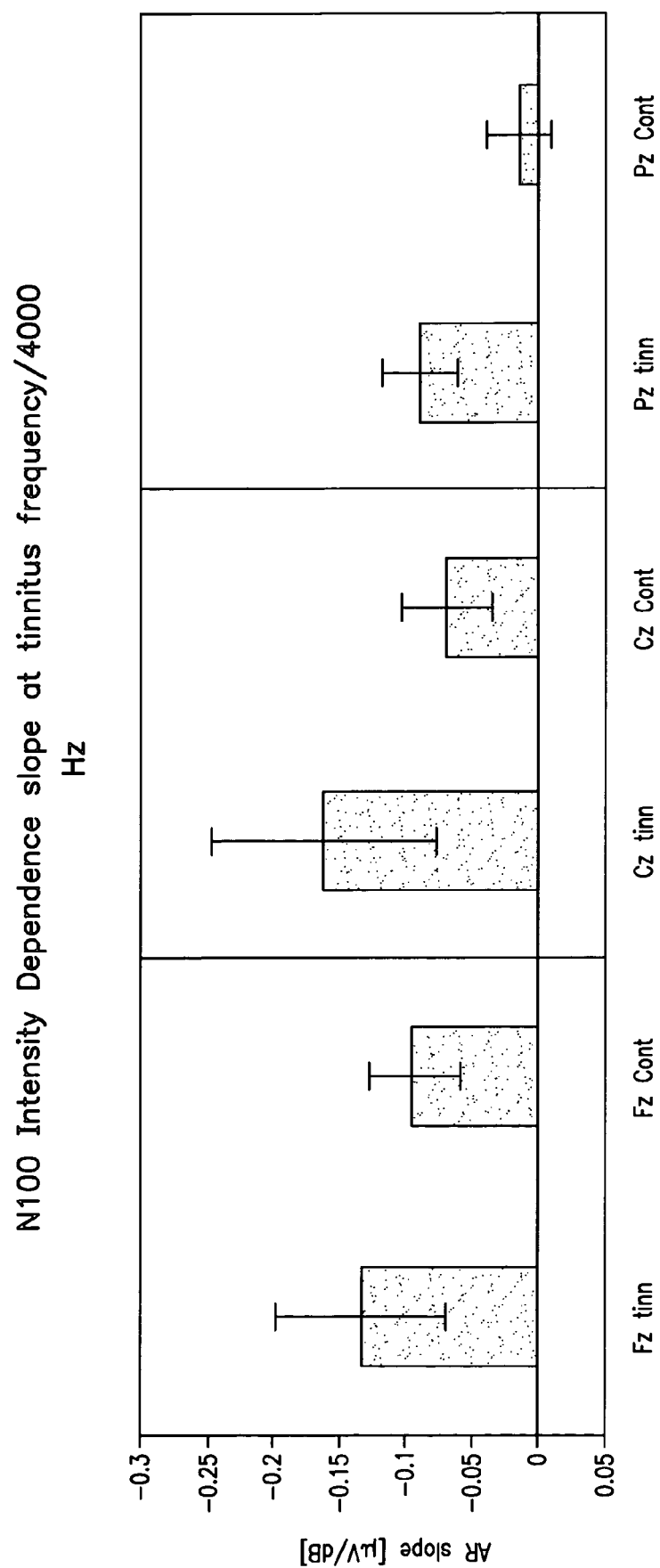

The results of the audiometric testing are shown in Table 1. An example of the N100 waveforms and its intensity-amplitude function is shown in FIG. 11. Comparison of the slopes of the intensity-amplitude functions between the tinnitus and control groups showed that the N100 responses from tinnitus patients to tones at their tinnitus frequency were slightly more intensity dependent (i.e., steeper slopes) than those of non-tinnitus controls to 4 kHz tones (FIG. 12C). In contrast, responses from the tinnitus group were significantly (p<0.05) less intensity dependent to 2 kHz tones than responses from the non-tinnitus control subjects (FIG. 12B). The intensity dependence of responses to 1 kHz tones is nearly identical in tinnitus and control subjects (FIG. 12A). Taken together these findings strongly suggest that tinnitus induces specific changes to N100 intensity dependence.

Discussion

The present results support the hypothesis that the presence of tinnitus related activity changes the intensity dependence of the N100 in a frequency

TABLE 1

| | | Right | | | Left | |
|---|---|---|---|---|---|---|
| Hearing loss | 1 kHz | 2 kHz | 4 kHz | 1 kHz | 2 kHz | 4 kHz |
| Tinnitus Wnl | 7 | 6 | 4 | 8 | 7 | 3 |
| Mild | 1 | 1 | 1 | 0 | 1 | 5 |
| Mod | 0 | 1 | 3 | 0 | 0 | 0 |
| Control Wnl | 12 | 12 | 10 | 12 | 12 | 11 |
| Mild | 0 | 0 | 1 | 0 | 0 | 1 |
| Mod | 0 | 0 | 1 | 0 | 0 | 0 |

Abbreviations:
Wnl: Within normal limits;
Mod: Moderate specific manner. The experimental data show statistically significant reductions in the intensity dependence of the N100 in response to 2 kHz tones and a non-significant increase in the intensity dependence of responses to the tinnitus frequency tones (4 kHz tones). It is Inventors' contention that tinnitus related activity produces an increase in firing rate of neurons or activation of more neural substrate. This, we believe, is reflected in the enhanced intensity dependence to tones at that frequency. Furthermore, enhanced activation of this isofrequency region causes inhibition of neighboring regions via lateral inhibitory mechanisms. This is reflected in the reduced intensity dependence to neighboring tones.

Inventors' working model of tinnitus is drawn from a recently proposed neurophysiological model of the disorder [Jeanmonod, 1996] in which tinnitus arises as a consequence of thalamocortical dysrhythmias. More precisely, auditory nuclei in the thalamus interact to establish a reverberating loop in which neuronal activity originating from this reverberating loop gets transmitted to the auditory cortex, where it gives rise to the perception of tinnitus. Such reverberating loops are established through disinhibition of cells in the thalamus, which occurs when thalamic relay cells are hyperpolarized by a lack of normal depolarizing sensory input. The action potentials generated by this hyperpolarizing mechanism, or low threshold spikes (LTS), usually occur in rhythmic bursts.

A computational model of tinnitus recently proposed by Langner et al. [Langner, 1999] accounts for how a decreased auditory input resulting from a peripheral hearing deficit can give rise to a specific tinnitus pitch. According to this model, the detection of tinnitus-related activity is facilitated by mechanisms of lateral inhibition in the central auditory system. These act to confine the neural activity causing the phantom perception to regions representing distinct frequencies and increase the contrast between the tinnitus-related activity and the spontaneous activity in adjacent regions.

Another indication that tinnitus related activity is confined to certain isofrequency regions of the auditory cortex comes from the fact that most tinnitus perceptions have distinct pitch. Furthermore, this pitch is often related to the underlying pathology. For example, noise-induced tinnitus tends to have a pitch near 4kHz [Mitchell, 1984]. In cases where the tinnitus is perceived as tonal, tinnitus-related activity in the auditory cortex can be assumed to be limited to isofrequency regions that correspond to the tinnitus pitch. Consequently, the changes in the intensity dependence of the midline auditory N100 response can be expected to be frequency specific.

Based on these models, a likely explanation for Inventors' findings is that tinnitus-related activity in the 4 kHz isofrequency region gives rise to lateral inhibition and thereby inhibits responses from the adjoining 2 kHz isofrequency region of the primary auditory cortex. This produces decreased intensity dependence of the auditory evoked potential in response to 2 kHz tones. This lateral inhibition effect must be limited in range such that responses to tones that are sufficiently different from the tinnitus frequency are not affected. Indeed, the intensity dependence of responses to 1 kHz tones is nearly the same in tinnitus and control subjects. This last finding contrasts with the increased intensity dependence of the N1/P2 component reported by Norena et al. However, since the N1/P2 complex is thought to be generated by equivalent dipoles representing the primary and secondary auditory cortices, whereas the N100 observed in this study is thought to be generated by equivalent dipoles representing only the primary auditory cortex, the contribution of the secondary auditory cortex may contribute to the higher intensity dependence observed by Norena et al. Another factor that can be expected to influence the intensity dependence of the N100 is hearing loss. As shown in Table 1, about half of the tinnitus subjects had some hearing loss at their tinnitus frequency. This hearing loss could lead to recruitment, i.e. increased loudness growth in response to higher intensity stimuli. Recruitment may be an alternative explanation for the increased intensity dependence of the N100 response at the tinnitus frequency. However, hearing for the tinnitus subjects was less impaired at 2 kHz, i.e. an octave lower than the tinnitus, so that hearing loss cannot account for the changed dynamics in N100 responses to these tones. Furthermore, the effect of hearing loss, as described above would be to cause an increase of the N100 intensity dependence rather than the observed decrease.

Conclusions

The present results suggest that tinnitus related activity in the primary auditory cortex changes the characteristics of the N100 component of the auditory evoked potential in a frequency specific manner. In tinnitus subjects responses to tinnitus frequency tones are slightly more dependent on stimulus intensity than in controls, while responses to 2 kHz tones, i.e. approximately one octave below the tinnitus frequency are significantly less dependent on stimulus intensity. The lack of intensity dependence in responses to 2 kHz tones is most likely caused by lateral inhibition in the auditory cortex arising from the tinnitus related activity. The observed changes in the dynamic properties of the N100 response is a way of demonstrating tinnitus related activity in the central neural system and may provide the basis for an objective tinnitus diagnostic tool.

EXAMPLE II

Habituation Therapy

Procedures
Subject Evaluation.

Two groups of subjects are selected and evaluated: normal controls and subjects with tinnitus. They are evaluated initially to determine hearing thresholds, as well as tinnitus pitch and intensity levels. The audiologist technician conduct s these procedures. Subjects are initially screened at the Otolaryngology Clinic to ensure they have no serious physical or mental disorders, have no other auditory deficits, and do not take any medication or other substances, which may affect EEG recording. Care is taken to ensure a balance between male and female subjects. Group sizes according to study design.

Pure Tone Audiometry Procedure

Prior to ERP experiments or habituation therapy, all subjects will have their audiogram taken using standard clinical procedures. For tinnitus subjects the audiogram are repeated every 3 months during habituation therapy and after completing the habituation therapy.

Subjective Tinnitus Pitch/Intensity Determination

A subject's perception of his or her tinnitus is characterized prior to every recording session by matching the pitch of their tinnitus to the frequency of a sine tone and the loudness of their tinnitus to the volume of a sine tone that matches the pitch of the tinnitus.

The following constitute typical instructions given to the subjects: "You are going to match a tone presented through the earphone or the speaker to the tone of your tinnitus for pitch/loudness. Every time that this tone is presented, I want you to compare it to your tinnitus tone and report that the presented tone is either:

"higher in pitch/loudness than your own tinnitus tone, equal to your own tinnitus tone, or lower in pitch/loudness to your own tinnitus tone"

In Inventors' experience matching the pitch of the tinnitus to the frequency of a sine tone has proven to be vulnerable to octave confusions, i.e. the tinnitus subjects match their tinnitus pitch consistently at two different frequencies, depending on whether the matching procedure was begun at a frequency higher or lower than their tinnitus pitch. These frequencies are usually roughly one or roughly two octaves apart. If this is the case, Inventors present both tones to the subject and ask which one is a better match.

Tinnitus Masking Level Determination

The tinnitus masking level is the level of the external stimulus tone that masks the tinnitus, according to the subject. This should be a level just above the reported tinnitus intensity level. Stimulus tones are initially presented at an intensity level below the determined intensity level of the tinnitus (this could even be at HL-5 dB). Subjects are given instructions similar to those described previously. For example, "you are going to tell me when you can no longer hear your own tinnitus. Every time that a stimulus tone is presented at a certain loudness, I want you to make a decision as to what you hear and report:

"I hear my tinnitus only".

"I hear both the stimulus tone and my tinnitus".

"I hear the stimulus tone only".

The masking level is the lowest intensity at which the subject reports that they only hear the stimulus tone. The procedure is repeated once or twice for reliability.

EEG Procedures

In order to detect tinnitus-related changes in the processing of auditory stimuli in the central auditory system, the auditory evoked potential is recorded. This involves the recording and analysis of EEG and ERPs. EEG is collected using standard methods. Data are recorded from 15 electrode sites mounted on an elastic cap and located over a variety of scalp sites (F3, Fz, F4, C3, Cz, C4, P3, Pz, P4, T3, T4, T5, T6, O1, and O2 according to the modified International 10-20 System). Eye movement artifacts, particularly blinks, are recorded from vertical and/or horizontal EOG electrodes. In order to maintain backward compatibility with previous studies, e.g. [Norena et al, 1999], and because Inventors' preliminary experiments show that the N100/P200 complex is best seen with referencing to linked mastoids, all electrode sites are referred to linked mastoids. Within each series, 80 stimuli of different intensities, for a total of 400 stimuli, are presented in random order and at intervals varying randomly between 1 and 3 sec. Inventors are aware that a better signal to noise ratio would be achieved with more stimulus presentations. However, for the purposes of this study, their preliminary experiments show the signal-to-noise ratio to be sufficient (see FIG. 3).

The EEG is amplified by 10K and bandpass filtered between 0.01 to 100 Hz at 3 dB down. Analog signals are recorded and digitized at a sampling rate of 250 Hz. For stimulus presentation and data acquisition and analysis, the ADAPT scientific software ((c) A. Vankov, 1997) or Neuroscan software is used. Both of these software packages permit the delivery of complex stimulus patterns and simultaneous data collection and analysis.

Auditory Stimulation

The auditory stimulations are sine waves generated by a function generator (Goldstar FG2002C). The intensity and the duration of each stimulus are set by a specially designed programmable logarithmic amplifier that is controlled in real time by a stimulus presentation and data collection program running in ADAPT. Auditory stimuli of five different intensities are presented through insert earphones (Eartone 3A transducers with Earl link foam eartips). In one stimulation series, the tone frequency is the subjectively assessed frequency of the subject's tinnitus. Three more stimulation series with stimulus frequencies at 1 kHz, 2 kHz and 8 kHz are carried out. In all series, tones are of 200 ms duration and varying in intensity (+30 dB, +36 dB, +42 dB, +48 dB, and +54 dB above the subject's hearing threshold at that frequency). For normal controls the auditory stimulation consists of series using 1 kHz, 2 kHz, 4 kHz, and 8 kHz, i.e. the stimulation series using the tones of the tinnitus frequency is substituted by one using 4 kHz tones.

Experimental Paradigm

On the day of testing, the sequence of the procedures is as follows:

1. In tinnitus subjects: Determine the "matching frequency" (pitch) of the subject's tinnitus. Subjects are presented with a continuous, audible tone varying in pitch. They are asked to indicate the frequency that most closely matches the frequency of their tinnitus. Several runs are used to determine the mean of the reported frequencies. Pitch matching is done in audiometrics.

2. In tinnitus subjects: Determine the hearing threshold for the tinnitus frequency. Subjects are presented with a continuous tone that gradually increases in volume. They are asked to indicate when they begin to hear the tone. The intensity at which the subjects begin to hear the tone is considered the hearing threshold (0 db). For EEG recording, tones at the tinnitus frequency are presented at volumes 30 dB, 36, dB, 42 dB, 48 dB, and 54 dB above this hearing threshold. Several runs are used to determine the subject's hearing threshold.

3. In tinnitus subjects: Determine the "matching intensity" of the subject's tinnitus. Subjects are presented with a continuous tone that increases or decreases in volume. They are asked to indicate the moment when they perceive the tone as being of the same loudness as their tinnitus. Several runs are used to determine the mean of the reported intensities. Masking level is determined in audiometrics.

4. Determine the hearing threshold for the "off frequencies. The same procedure as in (2) is used, but with 1 kHz, 2 kHz, and 8 kHz tones (in control subjects: 1 kHz, 2 kHz, 4 kHz, and 8 kHz tones). For EEG recording, these tones are presented at volumes 30 dB, 36, dB, 42 dB, 48 dB, and 54 dB above this hearing threshold.

Following the determination of the tinnitus pitch and intensity and subject's hearing threshold, one series of tonal stimulation and EEG collection takes place at each stimulus frequency. The series are presented in random order determined with a dice.

EEG Data Analysis

In one embodiment, the EEG data are analyzed using a two-stage approach. In the first stage, they are artifact-rejected. Initially, traditional artifact rejection is employed to remove trials with amplifier blocking and those that contain eye blinks. In the second stage, the remaining single trials are concatenated and submitted to an ICA decomposition. Components that account for eye, muscle, or movement artifacts are selected and those rows in the activation matrix are set to zero. The data are then reconstructed without the artifacts (for a detailed description of the ICA algorithm and how it is applied to correct for EEG artifact, see [Makeig et al, 1997]; [Makeig et al, 1999]). The artifact-free EEG epochs for each intensity and condition are averaged and the amplitudes of the N100 components measured. Based on these data, intensity-amplitude functions are computed for all 15-electrode sites. These are used to characterize an individual's responsiveness to specific tonal frequencies and as the measure of changes in that responsiveness.

EXAMPLE II

EEG Index of Tinnitus

Inventors determined whether N100 intensity dependence (i.e., the changes in amplitude in this brain signal as a function of stimulus intensity) differs in tinnitus sufferers compared to non-tinnitus control subjects. The experiment thus far has involved 24 tinnitus subjects and 14 control subjects. Tinnitus subjects were initially asked to match the pitch of their internal tinnitus to the frequency of a sine tone. Auditory ERPs in response to tones of up to four frequencies were recorded. For the non-tinnitus control subjects, these frequencies were 1 kHz, 2 kHz, 4 kHz and 8 kHz. In tinnitus subjects, their own tinnitus frequency was substituted for one of the frequencies used with the control subjects. For all subjects, tone pips were presented at intensities of 30 dB SL, 36 dB SL, 42 dB SL, 48 dB SL and 54 dB SL. The peak amplitudes of the N100 component were then measured and plotted as a function of stimulus intensity. A linear regression was calculated, and its slope used to characterize the intensity dependence of the N100 component (see FIG. 11).

The resulting data from a subset of the tinnitus group, i.e., those subjects whose tinnitus pitch was near 4 kHz, show significantly higher intensity dependence of the N100 compared to controls (see FIG. 12). Furthermore, comparison of the N100 intensity dependence of the tinnitus and control subjects showed that the N100 responses from tinnitus patients to 2 kHz tones was significantly less intensity dependent (i.e., smaller slopes) than those of non tinnitus controls (Wilcoxon-Mann-Whitney U-test, $p<0.05$). In contrast, responses from the tinnitus group were slightly more intensity dependent to their tinnitus frequency tones (which had a mean of 4.2 kHz) than responses to the 4 kHz from the non-tinnitus control subjects.

Audiograms were taken from all of the tinnitus subjects and 11 of the control subjects. Two of the tinnitus subjects had mild and one had moderate hearing loss at their tinnitus frequency. The hearing loss observed at the tinnitus frequency makes it possible that the stronger intensity dependence observed in the responses of tinnitus patients to tinnitus frequency tones may have been caused by recruitment (abnormal loudness growth) rather than tinnitus. However, the weaker intensity dependence observed in responses to 2 kHz tones is opposite of the effect of recruitment, and thus not attributed to it. Inventors attribute this effect on intensity dependence to the lateral inhibition caused by the tinnitus-related activity in the auditory cortex.

EXAMPLE III

Customized Habituation Therapy with Habituation Stimuli

Figure 7:
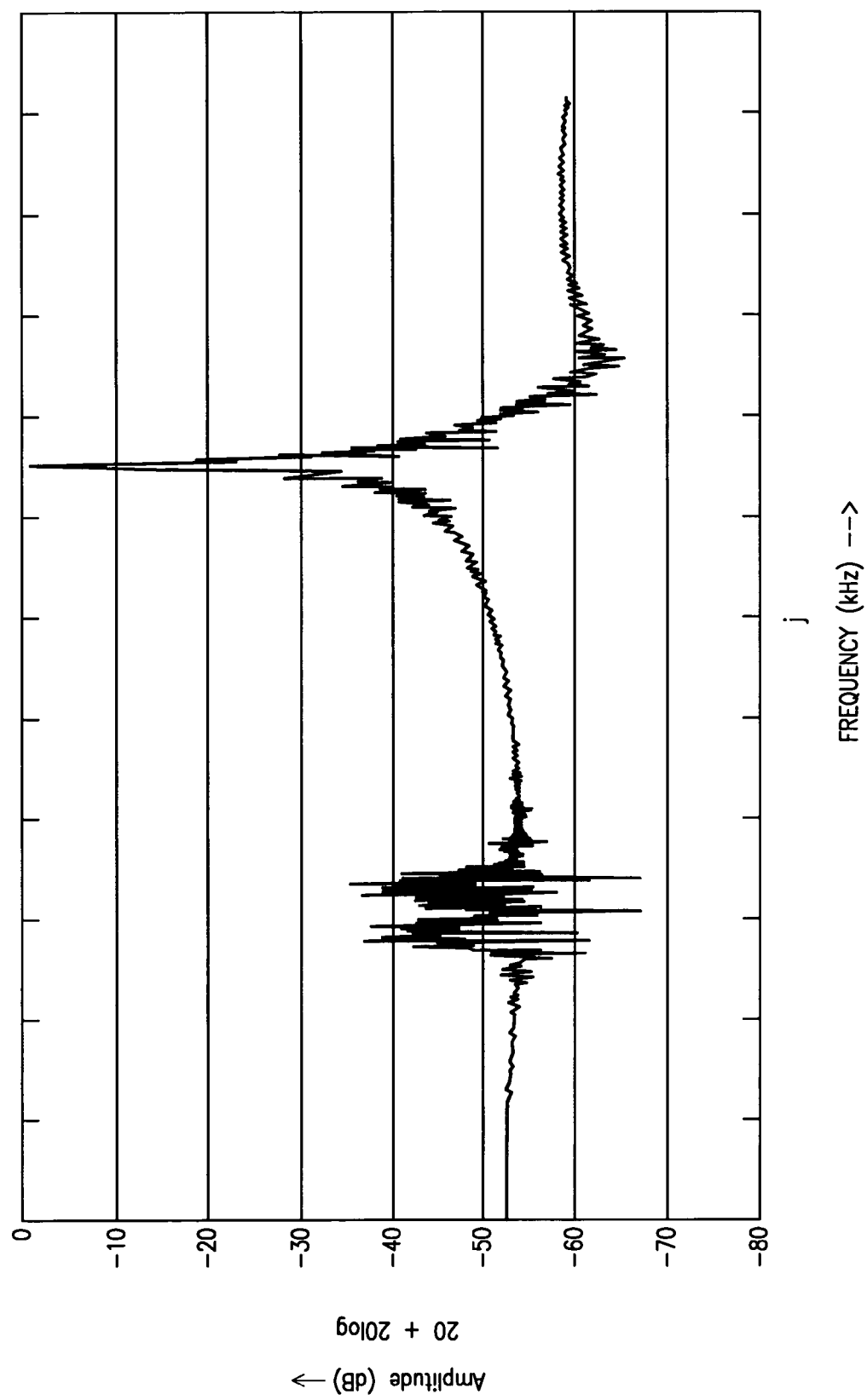
FIG. 7 is a spectrogram of a typical tinnitus habituation stimulus, showing two closely-spaced narrow band noises centered at 2800 and 3225 Hz, and a very narrow band noise centered at 7417 Hz which is almost 40 dB stronger than the first two.

Although their judgements are necessarily subjective, tinnitus subjects have evinced excellent consistency when it comes to matching habituation sounds with their tinnitus. Before beginning the habituation therapy, Inventors required subjects to confirm that the habituation sound matched their tinnitus at two or more sessions separated by at least a week. While there is some evidence that adjustments in the habituation stimulus may be desirable after habituation has progressed a few weeks, it seems reasonably clear, that this is due to changes in the characteristics of the tinnitus itself rather than a mismatch in the habituation sounds. The frequency content of a typical habituation stimulus is shown in FIG. 7.

Figure 8:
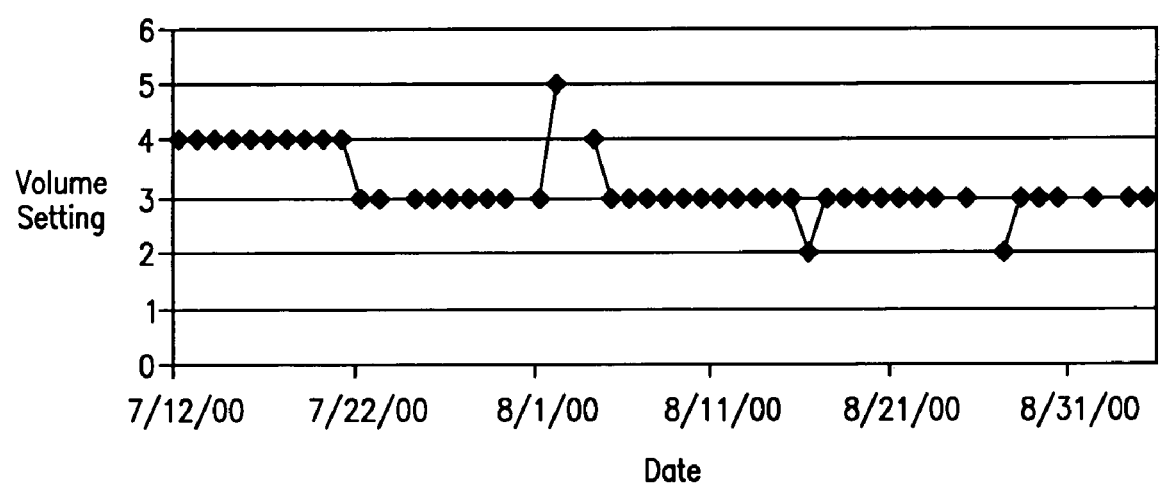
FIG. 8 displays typical volume settings on the MPEG player used during habituation training.

Tinnitus retraining therapy requires habituation to constant noise exposure. In order for habituation to occur, the habituation stimulus has to be audible, but must not be so loud as to mask the tinnitus [Jastreboff et al, 1996]. Therefore, the volume setting that a tinnitus subject uses on their noise generator gives an estimate of the loudness of the tinnitus. The volume settings that Inventors' tinnitus subjects used during this experiment decreased over time, in one case so much that the subject exhausted the available volume settings and the stimulus had to be resynthesized at a lower intensity (FIG. 8).

Figure 9:
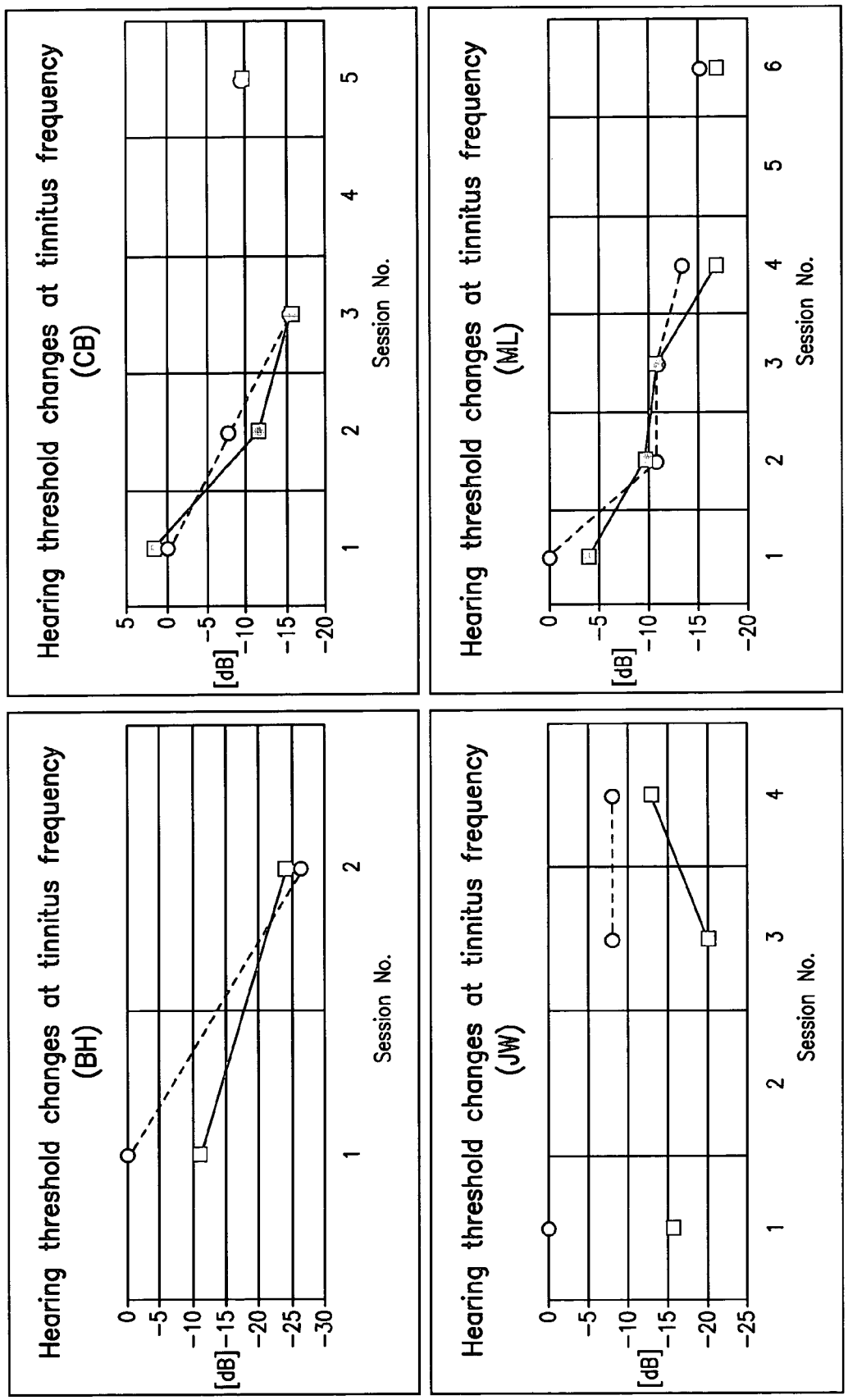
FIG. 9 shows hearing thresholds of tinnitus patients before and after habituation.

Since the experimental recording procedure required a determination of the hearing threshold every time a recording of an auditory evoked potential was made, Inventors have records of the changes to the hearing thresholds during habituation therapy. Hence, in a typical recording session, subjects had their hearing threshold determined and auditory evoked potentials recorded at their tinnitus frequency and at 1 kHz. Subjects then listened to their customized habituation stimulus for an hour and the determination of the hearing thresholds and the recording of the auditory evoked potential was repeated. Within a session, the hearing threshold at the tinnitus frequency was lowered by as much as 15 dB. Over several weeks of habituation training, hearing thresholds at the tinnitus frequency were observed to decrease by as much as 25 dB (FIG. 9).

Habituation training caused changes in the intensity dependence of the N100 amplitude as well as N100 latencies of tinnitus subjects. Before exposure to customized habituation stimulus the amplitude of the N100 component of the response to a tinnitus frequency tone was much more intensity dependent than the N100 component in response to a 1 kHz tone. Likewise, the N100 latencies increased with increasing stimulus volume. After subjects listened to the habituating stimulus for one hour, the intensity dependence of the response to the 1 kHz tone increased, and the latency of the N100 component of the response to the tinnitus frequency tone decreased with increasing stimulus volume (FIG. 4). Normal hearing control subjects were exposed to a stimulus similar to the habituating one for the tinnitus patients. The stimulus used in these control experiments was a narrow noise band with a center frequency of 4 kHz. Neither the intensity dependence of N100 amplitude or latency were changed by the exposure to the control stimulus (FIG. 5). Taken together, these findings suggest that the exposure to the habituating stimulus has an effect on tinnitus related activity in the auditory cortex of the tinnitus subjects. A single one-hour exposure, however, is not enough to make the pattern of intensity dependence similar to the one observed in normal controls.

Habituation training in conjunction with directive counseling has been shown to be an effective treatment for tinnitus [Jastreboff et al, 1996b]. Typically, white noise is used as the habituating stimulus in tinnitus retraining therapy (TRT). White noise evokes stimulus-induced neural activity in all of the parallel frequency-specific channels in the auditory system and is therefore likely to cause activity in those populations of neurons that also show tinnitus-induced activity. For habituation training, it may be sufficient to excite a much smaller population of neurons, namely those that are contributing to the tinnitus. A physical stimulus targeting these neurons would induce a similar perception as the tinnitus, i.e. sound like the tinnitus. Inventors propose to synthesize stimuli to match the patient's tinnitus and use this sound for habituation training. By recording the patient's auditory evoked potentials, Inventors can quantitatively describe the changes in the electrophysiological markers induced by the habituation. Further, Inventors will record the changes in audiometric tests as well as in subjective tinnitus measures.

Habituation therapy as proposed by Jastreboff [Jastreboff et al, 1996b] has been shown to achieve an 84% success rate in patients in terms of decreased annoyance induced by tinnitus and showing clear habituation of its perception.

Jastreboff claims that habituation therapy using white noise as a habituation stimulus causes the signal-to-noise ratio between the tinnitus related activity and spontaneous activity in the central auditory system to decrease. At the same time, the central auditory system undergoes a habituation to the permanent presence of an auditory stimulus. This habituation should lead to a decrease in tinnitus-related activity and consequently to decreased tinnitus perception and annoyance. However, descriptions of tinnitus perception and Inventors' preliminary results indicate that the tinnitus perception and the perception caused by white noise are very different from each other. When white noise is used for habituation therapy, two distinct continuous auditory perceptions are present. One is the behaviorally irrelevant, stimulus-driven perception of the white noise, the other is the tinnitus, a highly annoying phantom perception. In these conditions, habituation is likely to occur, but it is habituation to white noise rather than to the tinnitus perception.

Inventors' approach is designed to produce a habituation to the tinnitus sound, by making the perceptions of the tinnitus sound and the habituating stimulus as similar as they can possibly be. This is done by using a customized sound that mimics the tinnitus perception as a habituation stimulus.

Thus, the perceptions experienced by Inventors' subjects are very similar, allowing the habituation to the customized habituation stimulus to extend to the tinnitus. In this part of the study Inventors test whether this approach is an effective treatment of tinnitus, i.e. causes tinnitus related annoyance to disappear, and whether the electrophysiological correlates of tinnitus described in Example I are changed as a consequence of this treatment.

Subjective tinnitus Pitch/Intensity Determination

The subjective experiences of tinnitus are characterized by Dr. Moore using a successive approximation technique. Individual subjects are asked to verbally describe to a sound synthesis expert the "sounds" they experience using whatever vocabulary they possess for describing sounds. Musical training and experience on the part of the subject are particularly valuable in this process, since they provide a useful language in which sound characteristics can be verbally communicated. However, while musical training or experience is helpful, they are not necessary in order to achieve good and consistent tinnitus match. In response to the subject's statements, sounds are synthesized using high-precision, general-purpose sound synthesis software. At present Dr. Moore synthesizes the tinnitus sound according to the description provided by the subjects using the program "pcmusic" (see for example [Moore, 1990]). The resulting sound is then played back to the subject, who responds with suggested adjustments, such as altering the pitch, number of components, balance or quality of the synthetic sound. In response to these suggestions, the sound description file is modified, and the process is repeated until the subject reports that the synthesized sound matches well his or her subjective tinnitus experience. The digitized sound is then downloaded into a small portable digital sound playback device (MPEG-player) for use during habituation. The synthesized sound is completely documented by the description file together with the pcmusic program, as well as any number of post facto techniques, such as Fourier analysis. The time needed for this successive approximation procedure can vary, depending on the subject's ability to describe their own subjective experience of tinnitus, and their ability to characterize differences between the tinnitus they experience and the sounds being synthesized by the computer. Practical experience indicates that this can be done in about two or three 2-hour sessions devoted to accurately characterizing the subject's experience.

Tinnitus Masking Level Determination.

Determination of the tinnitus masking level is the same as in Example I.

EEG Procedures

EEG Procedures are the same as in Example I.

Auditory Stimulation

The auditory stimulation is similar to that used in Example I. Since the 1 kHz and tinnitus frequency tone are presented before and after habituation (see 'Experimental Paradigm' below), the 2 kHz and 8 kHz tones are not presented.

Experimental Paradigm

On the day of testing, the sequence of the procedures is as follows:

Determine the "Matching Frequency" (Pitch) of the Subject's Tinnitus.

Subjects are presented with a continuous, audible tone varying in pitch.

They are asked to indicate the frequency that most closely matches the frequency of their tinnitus. Several runs are used to determine the mean of the reported frequencies.

Determine the Hearing Threshold for the Tinnitus Frequency.

Subjects are presented with a continuous tone that will gradually increase in volume. They are asked to indicate when they begin to hear the tone. The intensity at which the subjects begin to hear the tone is considered the hearing threshold (0 db). For EEG recording, tones at the tinnitus frequency are presented at volumes 30 dB, 36, dB, 42 dB, 48 dB, and 54 dB above this hearing threshold. Several runs are used to determine the subject's hearing threshold.

Determine the "Matching Intensity" of the Subject's Tinnitus.

Subjects are presented with a continuous tone that will increase or decrease in volume. They are asked to indicate the moment when they perceive the tone as being of the same loudness as their tinnitus. Several runs are used to determine the mean of the reported intensities.

Determine the hearing threshold for the "off" frequency. The same procedure as above is used, but with a 1 kHz tone. For EEG recording, 1 kHz tones are presented at volumes 30 dB, 36, dB, 42 dB, 48 dB, and 54 dB above this hearing threshold.

Following the determination of the tinnitus pitch and intensity and subject's hearing threshold two series of tonal stimulation and EEG collection will take place. The first series is at the tinnitus frequency, while the second one is at the "off" tonal frequency (1 kHz).

At the end of the tonal series, subjects are exposed to 1-hr of habituation with customized habituation sound. The subjective "masking" threshold of the tinnitus is determined. They will then listen to the sound at 6 dB below the masking threshold for approximately 1 hour. The hearing threshold at the tinnitus frequency and at the "off" frequency is measured again at the end of the one-hour habituation. At the end of the habituation period and after a 2-minute break, two more series of tonal stimulation and EEG collection, identical to the ones described above, are conducted.

Subjects are given the MP3 player with the habituation stimulus and asked to listen to it for as long as it is comfortable each day. They are asked to return to the lab after one, four, and 12 weeks of habituation therapy for the same EEG evaluation.

Data Analysis

The EEG data are analyzed using the procedures described in Example I. When the slopes of the augmenting/reducing responses are calculated, Inventors look for changes within and between sessions. These changes are correlated to the behavioral data obtained during the experimental sessions.

Habituation therapy using white noise leads to an improvement in 83% of cases [Jastreboff et al, 1996b]. Therefore, an important question to be addressed in this aim is not only whether successful tinnitus treatment returns behavioral and EEG indices to normal or whether one type of therapy is faster than another but whether these parameters have predictive value in terms of treatment efficacy. This data analysis will also involve an analysis of all the data collected for Example I in order to develop a model that can make reasonable inferences and serve as a diagnostic tool to monitor habituation therapy. If there is a specific pattern of alteration, clinicians will have a reliable tool to help assess the effectiveness of these acoustic therapies.

Subject Populations.

Approximately 200 normal, healthy, ethnically diverse adults (aged 18-30), both male and female, who are recruited from the general student population at UCSD are studied each year. The population at UCSD is approximately 48% male and 52% female. The breakdown in terms of ethnicity is Caucasian (39%), Asian (30%), Mexican-American (8%), Filipino (5%), others (18%).

Subjects are recruited through bulletin board ads, email, announcements in undergraduate courses, and personal references. They are paid for their participation in the experiments on an hourly basis or compensated with credit toward undergraduate coursework. They are asked to read and sign a consent form approved by the Institutional Review Board (IRB). Subjects are made aware of the risks, which are minimal since all the hardware has been designed for this particular purpose, the stimuli are of low intensity and painless, and the subjects are not be placed under any stress. Any discomfort due to the skin abrasion and electrode gel may remain for a short while after the experiment is completed.

EXAMPLE IV

Altered Cortical Responses in Tinnitus Patients Following Habituation Therapy

Inventors examined short and long term effects of habituation to a customized sound. Habituation to a customized sound may have effects at both a behavioral and an electrophysiological level. Patients describe the effect of listening to their customized sound as comforting, saying for example that it helps them fall asleep or make them feel in control of their tinnitus. Patients give this feedback frequently within minutes after first turning on their MP3 players. In order to substantiate these patient testimonials, patients were asked to complete the 'Tinnitus Handicap Questionnaire before and after the three week habituation period. The questionnaire consists of 27 statements to which the patient responds by writing down a number between 0 and 100 next to each statement, where 100 means complete agreement and 0 complete disagreement with the statement. The questionnaire is constructed in such a way that high scores indicate more severe tinnitus than low scores. The questionnaire assesses the overall effect tinnitus has on the patient's life. It contains three subscales that measure the effects tinnitus has on more specific aspects of a patients life, namely their mental health, their ability to hear and their attitude towards tinnitus. So far three patients have completed the three week habituation protocol, giving the following scores:

TABLE 2

|  | Overall | Mental Health | Hearing | Attitude |
| --- | --- | --- | --- | --- |
| before | 11.2 | 17.9 | 5.0 | 5.0 |
| after | 5.6 | 5.7 | 1.7 | 5.0 |
| before | 50.0 | 67.9 | 29.2 | 37.5 |
| after | 37.0 | 53.2 | 23.3 | 27.5 |
| before | 48.8 | 68.6 | 23.3 | 40.0 |
| after | 48.0 | 64.3 | 37.5 | 25.0 |

Another way of assessing the effectiveness of the Customized Sound therapy is by observing the EEG correlate of tinnitus. We undertook a series of EEG experiments in which we measured the change of the intensity dependence of the amplitude and latency of the auditory N100 response as a consequence of one hour of habituation training. We recorded the responses to tinnitus frequency tones and 1 kHz tones from tinnitus patients and control subjects before and after one hour of habituation. Tinnitus patients used their customized sound for habituation, control subjects used narrowband noise with a center frequency of 4 kHz, and 4kHz tones were presented to substitute for the tinnitus frequency. Due to the small number of subjects in this study the results of these experiments do not reach statistical significance. However the provide an indication that the response pattern of tinnitus patients was changed by one hour of habituation (FIG. 4), while no such effect was observed in the control subjects (FIG. 5).

EXAMPLE V

Automatic Feedback Habituation System

Figure 10A:
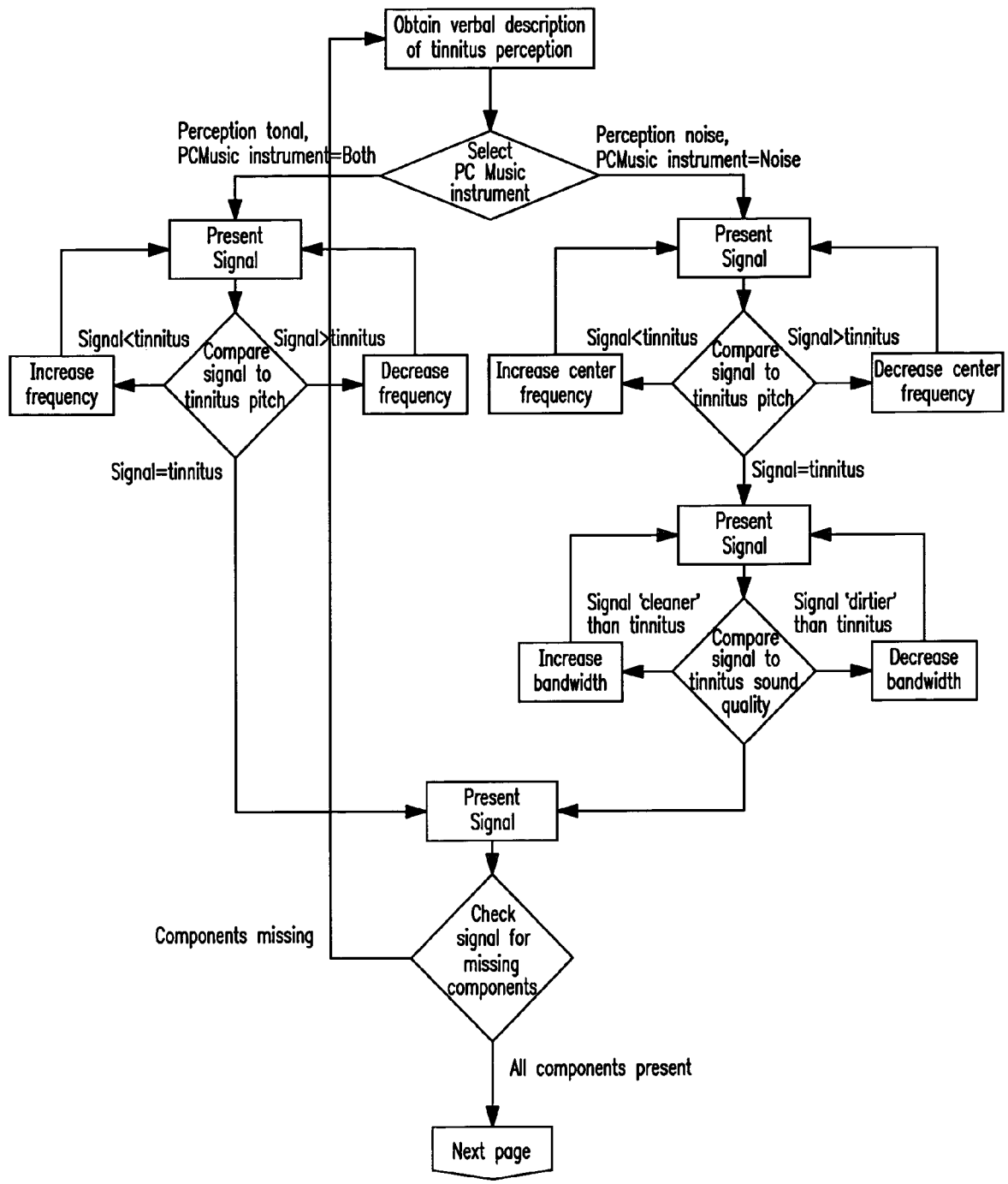
FIG. 10A and 10B is a flow diagram illustrating the steps of the creating the components and adjusting the components aspects of an automatic feedback habituation system.
Figure 10B:
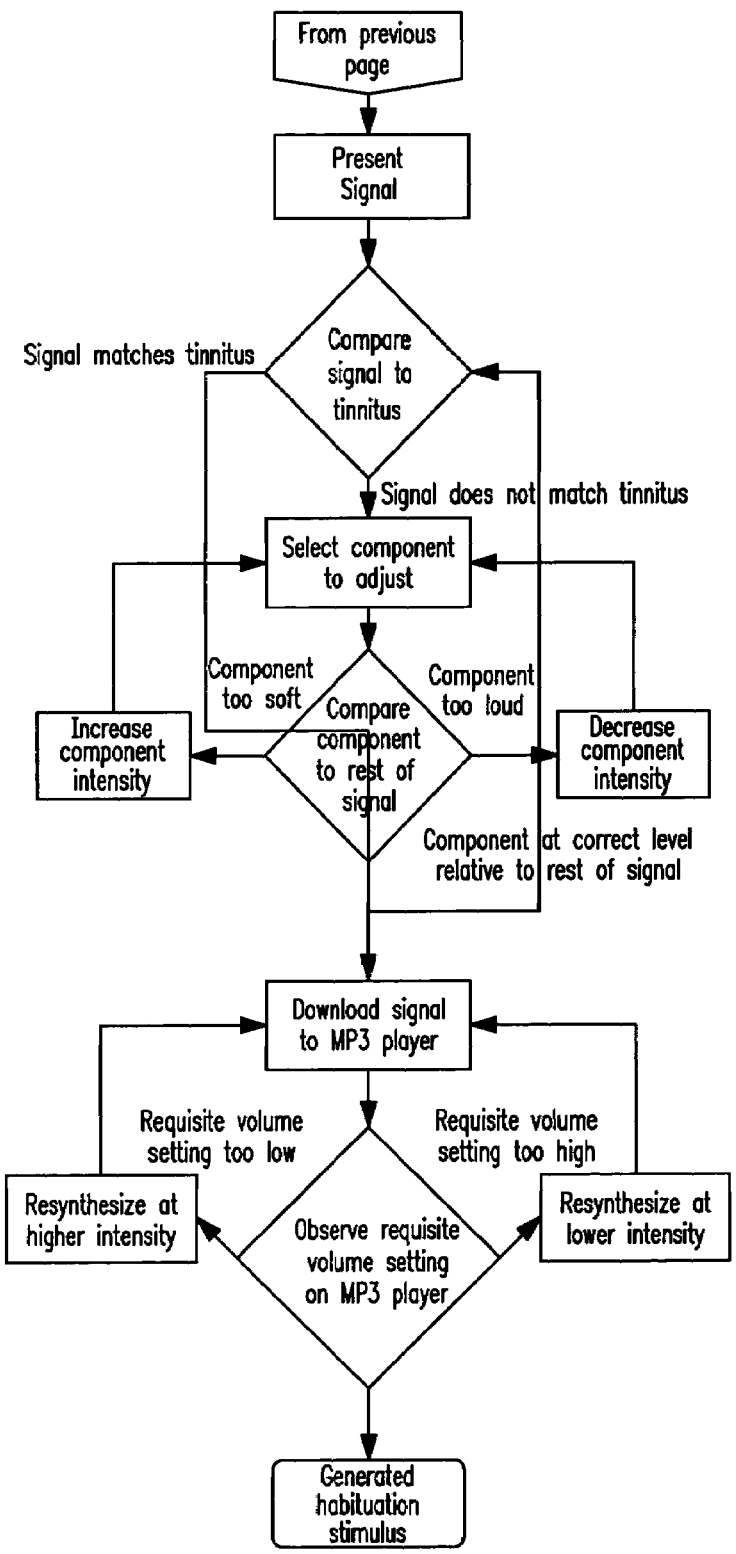

A flow diagram representing the steps involved is seen in FIG. 10. From this diagram, the novelty of the invention is clearly apparent. Subjects come to a PC workstation with electronic sound players. Software designed by an electronic sound expert presents a series of tones to the subjects and refines them to match the subjects' tinnitus experience through a series of controllers that the subjects will manipulate themselves. An electronic recording of the sound is then made in a digital music format, typically MP3 that is then stored on the computer. A copy of the electronic sound file is then transferred to the electronic music player. This device is solid state electronics that stores and plays back music through a set of attached headphones.

After the customized sound generation, an EEG signature of a subject's brain activity is generated. The customized sound is used to stimulate the auditory system while the brain activity is recorded. The subject's response to sounds not corresponding to their tinnitus signature is recorded, as well as their brain activity during the absence of sound stimuli. The EEG responses to sound stimuli and to the absence of sound are downloaded into the controlling computer. While the EEG is actively being monitored by the computer, it generates the customized sound. EEG signature for tinnitus is monitored as well as the signature for silence. Periodically, the signatures for tinnitus and silence are tested for and the controlling computer determines if the tinnitus is going down and the silence signal is strengthening. If these changes are not present, the computer slightly alters the sound stimuli and again checks for feedback that the appropriate changes are being seen. The computer continuously monitors for the feedback signatures and drives the sound stimuli appropriately.

The method of using brain signals to drive the sound generation for suppression of tinnitus is unique. Inventors assert that this method can likely be generalizable to a wide variety of medical conditions where input signals can be used to suppress brain activity and be maximized by brain signal feedback. For example, brain signatures for motion sensation and absence of motion could be used with visual motion generation to reduce chronic vertigo. Moreover, Parkinson's disease could suppressed by motor control stimuli and motor signal feedback, or depression could be suppressed by visual and auditory stimuli driven with EEG signature feedback.

The potential clinical application for this is the rapid treatment of tinnitus. Currently there are sound therapies for tinnitus that use generic sounds. The present therapies are only partially effective and require a long time. With the brain signal feedback system, we are rapidly able to suppress brain activity related to tinnitus and provide relief for this disorder.

In accordance with these and other possible variations and adaptations of the present invention, the scope of the invention should be determined in accordance with the following claims, only, and not solely in accordance with that embodiment within which the invention has been taught.

REFERENCES

Anderson, B. W. and Oatman, L. C. Auditory and Visual Evoked Potentials to Irrelevant Stimuli During Conditioning to a Visual Stimulus. Neurol. Res. 1980;1(3):281-90.

Bortz, J., Liehnert, G. A., and Boehnke, K, Verteilungsfreie Methoden in der Biostatistik, Berlin, Heidelberg, New York, London, Paris, Tokyo, Hong Kong, Barcelona, Springer Verlag, (1990).

Buchsbaum, M. and Silverman, J. Stimulus Intensity Control and the Cortical Evoked Response. Psychosom. Med. 1968;30(1): 12-22.

Connally, J. F. The Influence of Stimulus Intensity, Contralateral Masking and Handedness on the Temporal N1 and T Complex Components of the Auditory N1 Wave. Electroenceph. Clin. Neurophysiol 1993 ;86: 58-68.

Duncan-Johnson, C. C. and Donchin, E. On Quantifying Surprise: the Variation of Event-Related Potentials With Subjective Probability. Psychophysiology 1977; 14(5):456-67.

Eggermont, J. J. On the Pathophysiology of Tinnitus; a Review and a Peripheral Model. Hearing Research 1990;48 (1-2): 111-23.

Gonzalez-Lima, F. and Scheich, H. Neural Substrates for Tone-Conditioned Bradycardia Demonstrated With 2-Deoxyglucose. II. Auditory Cortex Plasticity. Behav. Brain Res. 1986;20(3):281 -93.

Hegerl, U., Juckel, G., and Möller, H. J. Event Related Brain Potentials As Indicators of Neurochemical Dysfunctions in Psychiatric Patients.

von Knorring, L. and Perris, C. Biochemistry of the Augmenting-Reducing Response in Visual Evoked Potentials. Neuropsychobiology 1981;7(1):1-8.

Wallhäusser-Franke, E., Braun, S., and Langner, G. Salicylate Alters 2-DG Uptake in the Auditory System: a Model for Tinnitus? Neuroreport 7-8-1996;7(10):1585-8.

Wilson, P. H., Henry, J., Bowen, M., and Haralambous, G. Tinnitus Reaction Questionnaire: Psychometric Properties of a Measure of Distress Associated With Tinnitus. Journal of Speech and Hearing Research 1991;34(1):197-201.

Wolpaw, J. R. and Penry, J. K. A Temporal Component of the Auditory Evoked Response. Electroencephalogr. Clin. Neurophysiol. 1975 ;39(6):609-20.

Woods, D. L. The Component Structure of the N1 Wave of the Human Auditory Evoked Potential. Electroencephalogr. Clin. Neurophysiol. Suppl 1995 ;44: 102-9.

Zuckermann, M., Mrtaugh, D, and Siegel, J. Sensation Seeking and Cortical Augmenting-Reducing. Psychophysiology 1974; 11:535-42.

What is claimed is:

1. An objective method for diagnosing tinnitus comprising:
   (a) determining a perceived tinnitus tone pitch of a subject;
   (b) recording an auditory evoked potential using an EEG machine of the subject to the tinnitus tone pitch and to at least one other tone pitch, wherein the tinnitus tone pitch and the at least one other tone pitch are individually played to the subject at a first intensity;
   (c) repeating step (b) with at least a second intensity;
   (d) calculating the slope of augmenting/reducing (AR) response of N100 for the tinnitus pitch and the at least one other tone pitch using data collection and analysis software, wherein an increase in the slope of the AR response to the tinnitus tone pitch is indicative of tinnitus, thereby diagnosing tinnitus.

2. The method of claim 1, wherein determining the perceived tinnitus tone pitch of the subject comprises:
   presenting the subject a continuous audible tone of varying pitch;
   determining which pitch is perceived by the subject as the tinnitus tone pitch, thereby determining the perceived tinnitus tone pitch of the subject.

3. The method of claim 2, wherein the continuous audible tone is a pure sine tone.

4. The method of claim 3, wherein the pure sine tone is generated by a function generator.

5. The method of claim 4, wherein the function generator comprises a programmable logarithmic amplifier that is controlled in real time by a stimulus presentation and data collection program to set the intensity of each tone.

6. The method of claim 1, wherein determining the perceived tinnitus tone pitch of the subject is performed using audiometrics.

7. The method of claim 1, further comprising the step of determining a hearing threshold of the subject to the perceived tinnitus tone pitch of step (a).

8. The method of claim 7, wherein the first intensity is 30 dB above the hearing threshold of the subject to the perceived tinnitus tone pitch.

9. The method of claim 1, wherein the subject perceives two tinnitus tone pitches that are one octave or two octaves apart.

10. The method of claim 1, wherein the at least one other tone pitch comprises 2 different tone pitches.

11. The method of claim 1, wherein the at least a second intensity comprises 5 different intensities.

12. The method of claim 1, wherein the tinnitus tone pitch is near 4 kHz, thereby diagnosing the tinnitus as noise-induced tinnitus.

13. The method of claim 1, wherein an increase in the slope of the AR response to the tinnitus tone pitch is indicative of tinnitus-related activity in the auditory cortex.

14. The method of claim 1, wherein 400 auditory evoked potentials are recorded.

15. The method of claim 1, wherein a series comprising 80 tone pitches are played to the subject at 5 different intensities each.

* * * * *

UNITED STATES PATENT AND TRADEMARK OFFICE
CERTIFICATE OF CORRECTION

PATENT NO. : 7,572,234 B2  Page 1 of 1
APPLICATION NO. : 11/292266
DATED : August 11, 2009
INVENTOR(S) : Viirre et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 633 days.

Signed and Sealed this

Seventh Day of September, 2010

David J. Kappos
*Director of the United States Patent and Trademark Office*